US010820864B2

(12) United States Patent
Peterson

(10) Patent No.: US 10,820,864 B2
(45) Date of Patent: Nov. 3, 2020

(54) METHODS AND SYSTEMS FOR PREDICTING PATIENT RESPONSIVENESS TO SUBCUTANEOUS NEUROMODULATION THERAPY AS A TREATMENT FOR HYPERTENSION

(71) Applicant: Valencia Technologies Corporation, Valencia, CA (US)

(72) Inventor: David K. L. Peterson, Valencia, CA (US)

(73) Assignee: Valencia Technologies Corporation, Valencia, CA (US)

( * ) Notice: Subject to any disclaimer, the term of this patent is extended or adjusted under 35 U.S.C. 154(b) by 675 days.

(21) Appl. No.: 15/057,106

(22) Filed: Feb. 29, 2016

(65) Prior Publication Data
US 2016/0256115 A1    Sep. 8, 2016

Related U.S. Application Data

(60) Provisional application No. 62/127,068, filed on Mar. 2, 2015.

(51) Int. Cl.
*A61B 5/00* (2006.01)
*A61B 5/021* (2006.01)
(Continued)

(52) U.S. Cl.
CPC ............ *A61B 5/7275* (2013.01); *A61B 5/021* (2013.01); *A61B 5/7246* (2013.01);
(Continued)

(58) Field of Classification Search
None
See application file for complete search history.

(56) References Cited

U.S. PATENT DOCUMENTS

| 5,615,684 A * | 4/1997 | Hagel ................. A61N 1/3621 600/513 |
| 8,805,512 B1 | 8/2014 | Greiner et al. |

(Continued)

*Primary Examiner* — Kaylee R Wilson
*Assistant Examiner* — Jay B Shah
(74) *Attorney, Agent, or Firm* — ALG Intellectual Property, LLC

(57) ABSTRACT

An exemplary method includes determining a variability of a plurality of measurements of a cardiovascular parameter of a patient suffering from hypertension, the plurality of measurements recorded one at a time over a predetermined time period. The method further includes comparing the determined variability with a predetermined reference value. If the comparing indicates that the determined variability is less than the predetermined reference value, the method includes designating the patient to be within a first class of patients representative of patients that are likely to be responsive to subcutaneous neuromodulation therapy as a treatment for hypertension. If the comparing indicates that the determined variability is greater than the predetermined reference value, the method includes designating the patient to be within a second class of patients representative of patients that are likely to be unresponsive to subcutaneous neuromodulation therapy as a treatment for hypertension. Corresponding systems and methods are also described.

20 Claims, 13 Drawing Sheets

(51) Int. Cl.
 *A61N 1/36* (2006.01)
 *A61N 1/05* (2006.01)
 *G16H 50/30* (2018.01)
 *G16H 20/40* (2018.01)
 G16H 20/10 (2018.01)

(52) U.S. Cl.
 CPC ........ *A61N 1/0504* (2013.01); *A61N 1/36117* (2013.01); *G16H 20/40* (2018.01); *G16H 50/30* (2018.01); G16H 20/10 (2018.01)

(56) References Cited

U.S. PATENT DOCUMENTS

| | | |
|---|---|---|
| 8,965,511 B2 | 2/2015 | Greiner et al. |
| 2002/0165586 A1* | 11/2002 | Hill .................... A61N 1/36114 607/9 |
| 2003/0135128 A1* | 7/2003 | Suffin .................... A61B 5/0006 600/544 |
| 2004/0111034 A1* | 6/2004 | Lin ...................... A61B 5/0002 600/485 |
| 2004/0204744 A1* | 10/2004 | Penner .................... G06F 19/00 607/23 |
| 2005/0288730 A1* | 12/2005 | Deem ................ A61B 18/1492 607/42 |
| 2007/0092888 A1* | 4/2007 | Diamond ............. C12Q 1/6883 435/6.11 |
| 2007/0265514 A1* | 11/2007 | Kiani ................ A61B 5/14542 600/365 |
| 2011/0172504 A1* | 7/2011 | Wegerich ............. A61B 5/0205 600/301 |
| 2013/0267469 A1* | 10/2013 | Matson ................ A61K 31/405 514/16.4 |
| 2014/0213890 A1* | 7/2014 | Razavi ................... A61B 5/065 600/424 |

\* cited by examiner

Overall Summary

| | AVG | STD | | MIN | MAX | Dipping |
|---|---|---|---|---|---|---|
| Systolic: | 145 | 16.41 | mmHg | 106 (09:16 Tue) | 183 (10:49 Mon) | 12.1% |
| Diastolic: | 76 | 11.98 | mmHg | 50 (00:16 Tue) | 117 (10:49 Mon) | 20.0% |
| MAP: | 100 | 13.23 | mmHg | 72 | 140 | 13.6% |
| Pulse Pressure: | 69 | 12.61 | mmHg | 43 | 100 | |
| Heart Rate: | 84 | 19.49 | bpm | 58 | 122 | |
| Percent of Systolic above limits: | | | | Reading(s) 89.2% | Time 87.5% | |
| Percent of Diastolic above limits: | | | | 8.1% | 6.1% | |

Wake Period(s) 06:00 - 22:00

| | AVG | STD | | MIN | MAX | |
|---|---|---|---|---|---|---|
| Systolic: | 149 | 15.11 | mmHg | 122 (10:16 Tue) | 183 (10:49 Mon) | |
| Diastolic: | 80 | 10.79 | mmHg | 67 (21:16 Mon) | 117 (10:49 Mon) | |
| MAP: | 103 | 12.52 | mmHg | 75 | 140 | |
| Pulse Pressure: | 69 | 13.87 | mmHg | 43 | 100 | |
| Heart Rate: | 89 | 18.37 | bpm | 58 | 122 | |
| Percent of Systolic readings > 135mmHg: | | | | Reading(s) 89.7% | Time 89.8% | |
| Percent of Diastolic readings > 85mmHg: | | | | 10.3% | 8.2% | |

Number of Wake Period(s) readings: 29

Sleep Period(s) 22:00 - 06:00

| | AVG | STD | | MIN | MAX | |
|---|---|---|---|---|---|---|
| Systolic: | 131 | 12.76 | mmHg | 106 (00:16 Tue) | 147 (05:16 Tue) | |
| Diastolic: | 64 | 6.66 | mmHg | 50 (00:16 Tue) | 70 (23:16 Mon) | |
| MAP: | 89 | 8.85 | mmHg | 72 | 97 | |
| Pulse Pressure: | 67 | 6.48 | mmHg | 56 | 77 | |
| Heart Rate: | 64 | 2.97 | bpm | 58 | 66 | |
| Percent of Systolic readings > 120mmHg: | | | | Reading(s) 87.5% | Time 85.5% | |
| Percent of Diastolic readings > 70mmHg: | | | | 0% | 0% | |

Number of Sleep Period(s) readings: 8

METHODS AND SYSTEMS FOR PREDICTING PATIENT RESPONSIVENESS TO SUBCUTANEOUS NEUROMODULATION THERAPY AS A TREATMENT FOR HYPERTENSION

RELATED APPLICATIONS

The present application claims priority under 35 U.S.C. § 119(e) to U.S. Provisional Patent Application No. 62/127,068, filed Mar. 2, 2015. The contents of the provisional patent application are hereby incorporated by reference in their entirety.

BACKGROUND INFORMATION

Hypertension, or high blood pressure, is a serious problem in the United States and worldwide. In recent decades, approximately one billion individuals have been diagnosed with hypertension as the availability of unhealthy and inexpensive foods has increased, sedentary lifestyles have become more common, and more people have become overweight or obese. People suffering from hypertension may have increased risks of stroke, angina, heart attack, and/or other life-threatening illnesses. Accordingly, along with regimented diet and exercise programs, various treatments have been developed to treat hypertension including pharmaceutical medications, nerve stimulation therapies (e.g., electrical stimulation of the vagal nerve, spinal cord, deep brain, etc.), and other treatments aimed at reducing blood pressure. While these treatments may work effectively in certain cases, they may also be ineffective and/or problematic. For example, pharmaceutical medications may have adverse side effects for certain patients, or patients may not respond to them. Similarly, nerve stimulation therapies have typically been aimed at crucial nerve centers of the body and have used types of electrodes (e.g., cuff-type electrodes, in-placement type electrodes, etc.) that are likely to cause irreversible nerve damage to these crucial nerve centers and often require relatively invasive and risky surgery to properly place.

An alternative treatment option for hypertension patients is subcutaneous neuromodulation therapy, in which a safe and relatively noninvasive implantable device is inserted subcutaneously into the patient's body at a known acupuncture site ("acupoint") and configured to perform electroacupuncture (e.g., acupuncture that applies electrical stimulation rather than needles to the acupoint) to treat the patient's hypertension. While research into the efficacy of electroacupuncture as a medical procedure is ongoing, traditional acupuncture (e.g., acupuncture in which needle-based stimulation is applied to the body's acupoints) has been used in Eastern cultures to treat various illnesses for millennia, and recent studies show that electroacupuncture performed by implanted electroacupuncture devices can be effective in treating hypertension and other conditions in certain patients.

As neuromodulation therapies are studied and implemented to treat patients with hypertension, it may be desirable to predict whether patients will be likely to be responsive to the neuromodulation therapy prior to surgically implanting the electroacupuncture devices in the patients and/or prior to enabling the implanted devices. For example, if one particular patient is likely to be unresponsive to subcutaneous neuromodulation therapy as a treatment for the patient's hypertension, the patient and/or a personal practitioner of the patient (e.g., a physician helping to treat the patient for hypertension) may wish for the patient to avoid certain inconvenience and/or costs associated with implanting the electroacupuncture device. Conversely, if it is known that a patient is likely to be responsive to the therapy, the patient and/or a personal practitioner of the patient may be more inclined to accept any inconvenience and/or cost that may be associated with implanting and/or enabling the electroacupuncture device to begin the therapy. Such predictions may also be useful for people studying the effectiveness of subcutaneous neuromodulation therapy as a treatment for hypertension because studies aimed at demonstrating the effectiveness of the therapy may be most successful and relevant when including only patients who are reasonably likely be responsive to the therapy to treat their hypertension.

Unfortunately, various factors currently analyzed to predict whether patients will be likely to respond favorably to treatment (e.g., biochemical markers such as norepinephrine spillover, sympathetic neural activity, patient demographics, patient response to medications, etc.) may involve specialized measurements requiring relatively high costs and special expertise not available in many patient centers, or may otherwise be overly inconvenient, costly, risky, or invasive to the patient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 9 illustrates an exemplary summary chart that summarizes, over several predetermined time periods, measurements of several cardiovascular parameters of a patient suffering from hypertension according to principles described herein.

DETAILED DESCRIPTION

Figure 1:
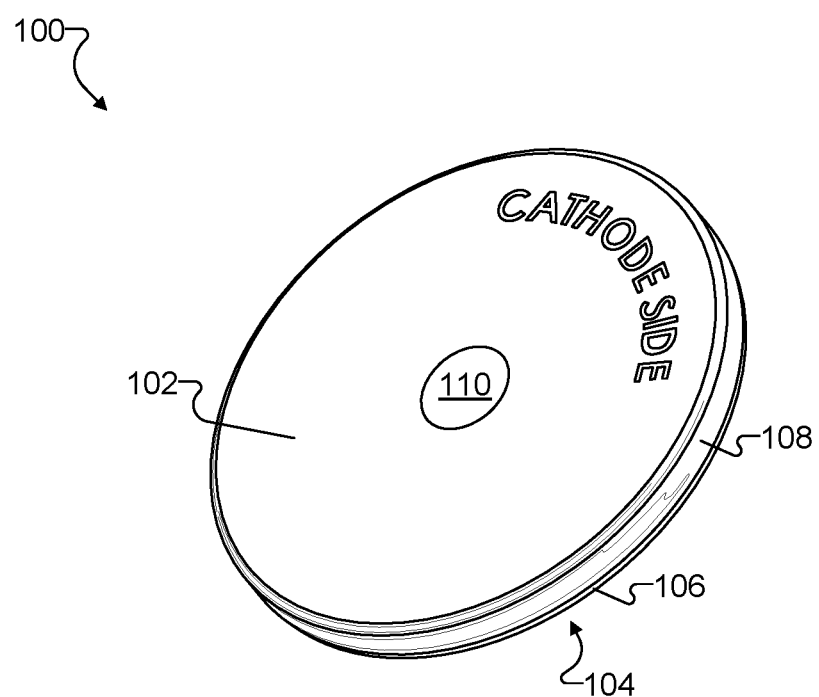
FIG. 1 illustrates a perspective view of a leadless implantable electroacupuncture device configured to be implanted subcutaneously within a patient and used to perform neuromodulation therapy as a treatment for the patient's hypertension according to principles described herein.

Methods and systems for predicting patient responsiveness to subcutaneous neuromodulation therapy as a treatment for hypertension are described herein. For example, an exemplary therapy response prediction system may be used to determine a variability of a plurality of measurements of a cardiovascular parameter (e.g., a systolic and/or a diastolic blood pressure) of a patient suffering from hypertension. The plurality of measurements may be recorded one at a time over a predetermined time period such as during a twenty-four hour period, or during waking hours of the patient during a single day. The therapy response prediction system may compare the determined variability with a predetermined reference value. If the comparison indicates that the determined variability is less than the predetermined reference value, the therapy response prediction system may designate the patient to be within a first class of patients. Alternatively, if the comparison indicates that the determined variability is greater than the predetermined reference value, the therapy response prediction system may designate the patient to be within a second class of patients. The first class of patients may be representative of patients that are likely to be responsive to subcutaneous neuromodulation therapy as a treatment for hypertension, while the second class of patients may be representative of patients that are likely to be unresponsive to subcutaneous neuromodulation therapy as a treatment for hypertension.

By designating different patients to be within different classes in this way, the therapy response prediction system may predict patient responsiveness to subcutaneous neuromodulation therapy as a treatment for hypertension in a way that is useful for patients and their personal practitioners, as well as for researchers conducting studies to demonstrate the effectiveness of subcutaneous neuromodulation therapy for at least certain groups of patients suffering from hypertension.

For example, methods and systems described herein may allow patients and their personal practitioners to make the best decisions possible regarding whether the patient should undergo surgery to implant an electroacupuncture device ("EA device") configured to perform the subcutaneous neuromodulation therapy. Patients designated to be within a class of patients that are likely to be unresponsive to subcutaneous neuromodulation therapy as a treatment for hypertension may choose to forego the therapy and the corresponding surgery, since inconveniences and costs associated with the surgery may outweigh potential benefits of the therapy. Meanwhile, patients designated to be within a class of patients that are likely to be responsive to the therapy may choose to undergo the therapy in spite of any inconveniences and/or costs associated with the surgery because the likelihood that the therapy will effectively treat their hypertension may outweigh the potential detriments associated with the surgery.

Moreover, methods and systems described herein may allow researchers conducting studies on the effectiveness of subcutaneous neuromodulation therapy as a treatment for hypertension to conveniently screen the most appropriate patients for particular studies, resulting in lower costs, easier and/or faster screening processes, and more effective studies. For example, previous studies have revealed that as many as one-third of potential hypertension patients may be unresponsive to subcutaneous neuromodulation therapy as a treatment for hypertension due to mechanisms particular to each patient that act to elevate that patient's blood pressure. Thus, by implementing a quick, convenient, inexpensive, and effective screening of patients in accordance with the methods and systems described herein, researchers conducting the studies may easily study the effects of the therapy on the approximately two-thirds of hypertension patients known to be most likely to actually respond to the therapy. Ultimately, by facilitating the studies in these ways, the methods and systems described herein may help subcutaneous neuromodulation therapy gain wider acceptance as a viable treatment for hypertension, leading to a wider availability of the treatment to help reduce life-threatening risks of hypertension for patients and practitioners who choose the therapy to treat hypertension.

Methods and systems for predicting patient responsiveness to subcutaneous neuromodulation therapy as a treatment for hypertension will now be described in relation to the figures. Additional benefits arising from the methods and systems will be made apparent in the description below.

FIG. 1 illustrates a perspective view of an exemplary leadless implantable EA device 100 configured to be implanted subcutaneously within a patient and used to perform neuromodulation therapy as a treatment for the patient's hypertension. For example, EA device 100 may be configured to treat hypertension through the application of electroacupuncture stimulation pulses at a specified acupoint of a patient near an implantation site of EA device 100. As shown, EA device 100 may have the appearance of a disc or coin (e.g., having a diameter of approximately 23 mm, and a thickness of approximately 2 to 3 mm), and may include a bottom side 102, a top side 104, and an edge 106. In order to function properly, EA device 100 may include various components located (e.g., hermetically sealed) within a housing of EA device 100 provided by bottom side 102, top side 104, and edge 106. For example, EA device 100 may include pulse generation circuitry configured to deliver electroacupuncture stimulation pulses to the patient's body tissue at the specified acupoint, a primary battery configured to provide operating power for EA device 100 to function, a communication subsystem (e.g., a coil and/or a sensor) for receiving and responding to operating commands wirelessly communicated to EA device 100 from a non-implanted location to externally control EA device 100 (e.g., to turn EA device 100 on or off, to adjust an amplitude of electroacupuncture stimulation pulses produced by EA device 100, etc.), and/or any other components that may serve a particular implementation.

To generate electroacupuncture stimulation pulses for the neuromodulation therapy, EA device 100 may also include an anode electrode 108 (e.g., a ring electrode) placed around a perimeter of edge 106, and a cathode electrode 110 centrally disposed on bottom side 102, as shown in FIG. 1. Additionally, an insulating later (not explicitly shown) may be included around edge 106 between edge 106 and anode electrode 108, and a layer of silicone molding (not explicitly shown) may cover some or all of the housing of EA device 100 (e.g., bottom side 102, top side 104, and edge 106). For example, silicone molding may be used to insulate the entire housing of EA device 100, leaving only anode electrode 108 and cathode electrode 110 exposed in order to better control electric fields established between anode electrode 108 and cathode electrode 110 and to prevent the entire housing of EA device 100 from acting as a cathode electrode.

As will be described in more detail below, in operation, EA device 100 may be implanted below the skin surface of the patient at a specified acupoint (e.g., PC5 or PC6 in the right or left forearm, S36 or S37 in the left or right leg shin, etc.) and may generate electroacupuncture stimulation pulses in accordance with a specified stimulation regimen. For example, the stimulation regimen may prescribe that a relatively short series of stimulation pulses be applied to the specified acupoint during a short session (e.g., a thirty minute session) that is separated by a relatively long period of time (e.g., seven days) from other stimulation sessions. As such, a duty cycle of the stimulation sessions may be very low (e.g., less than 0.05). Additionally, a duty cycle of the stimulation pulses applied during a stimulation may also be very low.

As shown, one advantage of EA device 100 may be a simple, leadless design. Specifically, electrodes 108 and 110 may be directly attached to the housing of EA device 100 rather than to leads configured to be positioned and anchored at desired stimulation sites away from the location that EA device 100 is implanted. As a result, implanting EA device 100 within a patient may be less invasive and/or less risky to the patient than implant procedures for implants having leads that must be tunneled through body tissue or blood vessels to reach desired stimulation sites.

Figure 2:
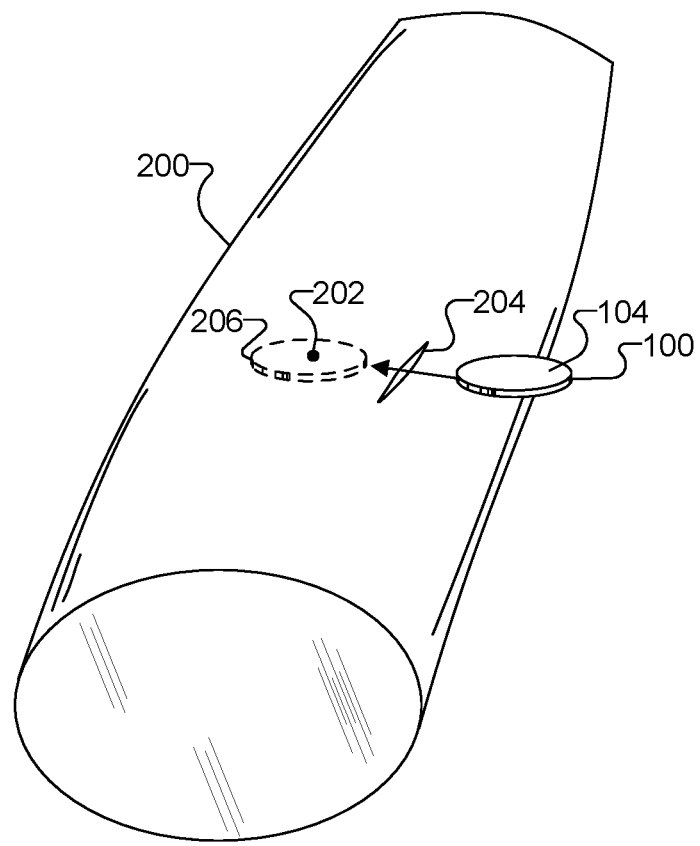
FIG. 2 illustrates a view of a limb of a patient where a specified acupoint has been identified and selected, and illustrates a manner of implanting an electroacupuncture device at the selected acupoint according to principles described herein.

To illustrate, FIG. 2 shows a view of a limb 200 of a patient (e.g., a forearm or shin of the patient). A specified acupoint 202 known to moderate or affect a hypertension condition of a patient (e.g., PC5 or PC6 in the forearm, or S36 or S37 in the shin) may have been identified and selected in limb 200 to receive electroacupuncture treatment. Accordingly, FIG. 2 illustrates a manner of implanting EA device 100 at acupoint 202 to provide the electroacupuncture treatment to acupoint 202. In particular, an incision 204 may be made into limb 200 near (e.g., 10 millimeters ("mm") to 15 mm away from) acupoint 202. A slot may be formed at incision 204 (e.g., by lifting up the skin closest to acupoint 202) and a pocket 206 may thus be formed under the skin at the location of acupoint 202 to receive EA device 100. Subsequently, with top side 104 facing up (i.e., facing the skin), EA device 100 may be slid through the slot of incision 204 and into pocket 206 so that EA device 100 is centered at specified acupoint 202. Then, with EA device 100 in place, incision 204 may be sewn up or otherwise closed and EA device 100 may be left under the patient's skin at the acupoint 202 location so that subcutaneaous neuromodulation therapy may be performed by applying the electroacupuncture stimulation pulses as described above. Advantageously, the implantation surgery of EA device 100 may often be completed in less than ten minutes in an outpatient setting or in a doctor's office. Only minor, local anesthesia may be used and no significant risks may be associated with the implant procedure. Also, if desired, EA device 100 may be quickly explanted in a similarly safe and easy surgical procedure.

Figure 3:
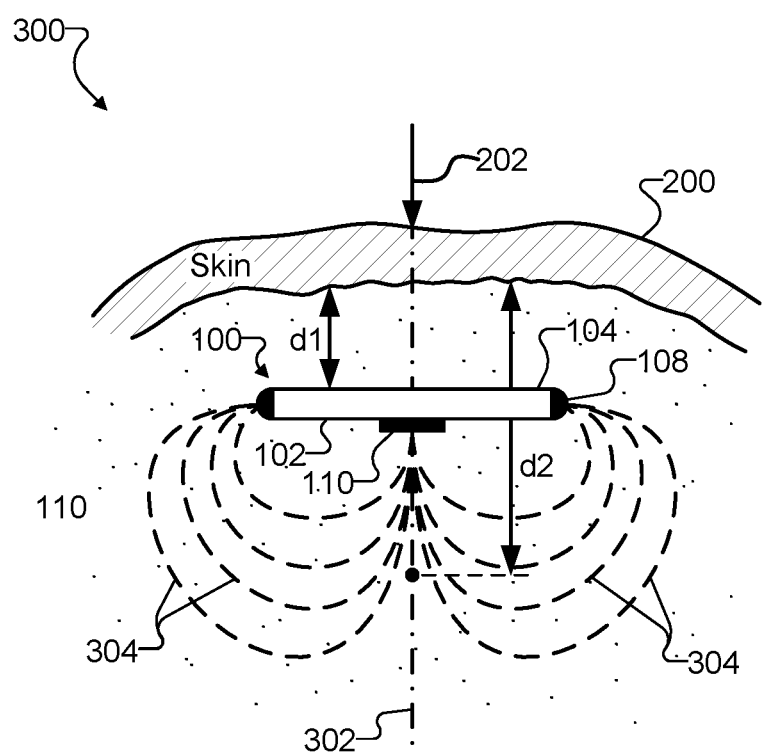
FIG. 3 illustrates a cross-sectional view of an exemplary electroacupuncture device implanted at a selected acupoint within a patient according to principles described herein.

FIG. 3 illustrates a cross-sectional view 300 of EA device 100 implanted at acupoint 202 within limb 200 of the patient. As shown, EA device 100 may be implanted at a depth d1 under the skin (e.g., approximately 2 mm to 4 mm under the skin). Top side 104 of EA device 100 may be facing up to the skin of the patient, while bottom side 102 of EA device 100, upon which cathode electrode 110 is disposed, may be facing down away from the skin. As illustrated by cross-sectional view 300, EA device 100 may provide a symmetrical electrode configuration where cathode electrode 110 is centrally located on an acupoint axis 302 extending orthogonally into the skin from a location on the skin where acupoint 202 is indicated, and where anode electrode 108, which may be implemented as a ring electrode, encircles cathode electrode 110 and acupoint axis 302.

The symmetry between cathode electrode 110 at the center and anode electrode 108 encircling cathode electrode 110 may help focus an electric field generated by electrodes 110 and 108, promoting stimulation current generated by application of an electroacupuncture stimulation pulse to flow into tissue below the central electrode, where it may be desired that electroacupuncture stimulation should be applied. For example, while acupoint 202 is illustrated in FIGS. 2 and 3 as being on the surface of the skin, electroacupuncture treatment may be most effective at a distance d2 below the skin surface along acupoint axis 302. The ideal distance d2 may vary depending upon where the acupoint is located on the body and depending on an aim of the acupuncture treatment to be performed. For example, for treating hypertension, depth d2 may be most effective between approximately 6 mm and 10 mm below the skin surface if acupoint 202 is in the forearm (e.g., acupoints PC5 and/or PC6), and between approximately 1 centimeter ("cm") and 2 cm below the skin surface if acupoint 202 is in the leg (e.g., acupoints ST36 and/or ST37).

Also illustrated in view 300 are electric field gradient lines 304, which may be created by an electroacupuncture pulse applied to tissue within the patient by anode electrode 108 and/or cathode electrode 110. As shown, electric field gradient lines 304 are strongest along a line coinciding with, or near to, acupoint axis 302. Accordingly, FIG. 3 illustrates that one of the primary advantages of the symmetrical electrode configuration of EA device 100 is that the precise orientation of EA device 100 within the patient is not important. Rather, as long as EA device 100 is centered at acupoint 202 (i.e., such that acupoint axis 302 passes through the center of EA device 100) and cathode electrode 110 is facing down, a strong electric field (e.g., illustrated by electric field gradient lines 304) may be generated to align with acupoint axis 302. As a result, EA stimulation current may flow along (or very near) acupoint axis 302, and the desired electroacupuncture stimulation may properly be applied to the tissue at a depth d2 below the acupoint 202 location indicated on the skin.

Various other configurations and implementations of EA device 100 may also be possible in particular implementations. For example, U.S. Pat. No. 8,805,512 ("the '512 Patent") and U.S. Pat. No. 8,965,511 ("the '511 Patent") both describe additional systems and methods for designing, manufacturing, implementing, and using devices similar to EA device 100 to apply electroacupuncture stimulation to patients' acupoints. As such, the '512 Patent and the '511 Patent are hereby incorporated by reference in their entireties. It will also be recognized that other types of implantable stimulators (e.g., implantable stimulators with leads connected thereto) may be used in accordance with the methods and systems described herein.

Figure 4:
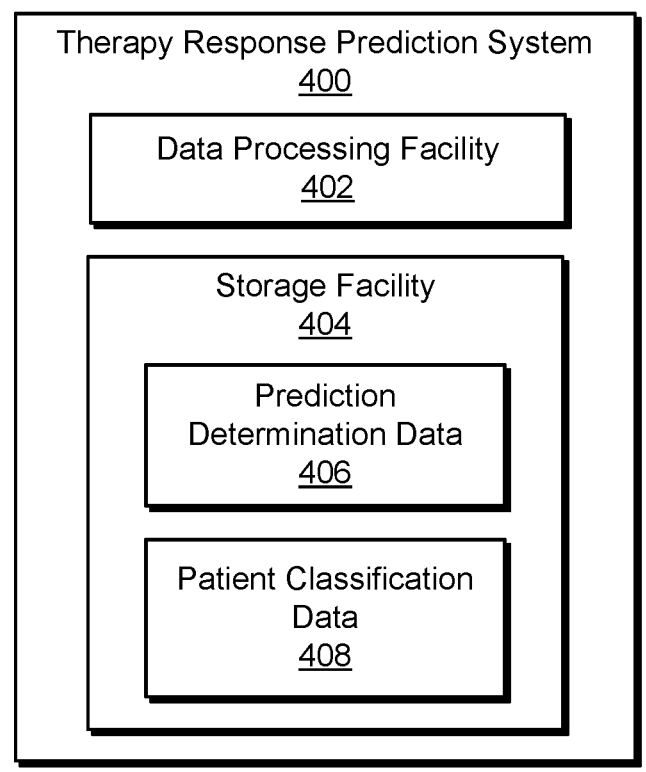
FIG. 4 illustrates exemplary components of a therapy response prediction system according to principles described herein.

FIG. 4 illustrates exemplary components of a therapy response prediction system 400 ("system 400"). System 400 may be configured to perform any of the operations described herein. As shown, system 400 may include a data processing facility 402 and a storage facility 404, which may be in communication with one another using any suitable communication technologies. Storage facility 404 may maintain prediction determination data 406, which may include any data generated, received, analyzed, and/or used by data processing facility 402 to generate predictions regarding the likelihood of one or more patients to be responsive to subcutaneous neuromodulation therapy as a treatment for hypertension.

Storage facility 404 may further maintain patient classification data 408, in which classifications related to predictions made by data processing facility 402 may be stored. For example, patient classification data 408 may include data related to each patient in a plurality of patients (e.g., patients associated with a particular clinic or office, patients associated with a particular practitioner, patients associated with a particular study, etc.). Along with other data related to a particular patient (e.g., the patient's name, contact information, medical history, etc.), patient classification data 408 may include a computer-readable value (e.g., a binary value) representative of a determination by system 100 (e.g., by data processing facility 402) regarding whether the patient is likely to be responsive to the subcutaneous neuromodulation therapy as a treatment for hypertension. In other examples, patient classification data 408 may include data structured according to classes of patients, such as by including data structure representative of a first class of patients representative of patients that are likely to be responsive to subcutaneous neuromodulation therapy as a treatment for hypertension and another data structure representative of a second class of patients representative of patients that are likely to be unresponsive to the therapy. Within a data structure representative of each class, data (e.g., a name, a blind identification number, etc.) representative of one or more patients may be stored to track which patients are designated to the class. Storage facility 404 may maintain additional or alternative data as may serve a particular implementation.

Data processing facility 402 may perform various operations associated with predicting patient responsiveness to subcutaneous neuromodulation therapy as a treatment for hypertension. For example, data processing facility 402 may determine a variability of a plurality of measurements of a cardiovascular parameter of a patient suffering from hypertension. The measurements of the cardiovascular parameter of the patient may be any suitable measurements. For example, in certain implementations, the measurements may include a measurement of a systolic blood pressure of the patient, a diastolic blood pressure of the patient, a mean arterial pressure ("MAP") of the patient, a pulse pressure of the patient, a heart rate of the patient, and/or any other cardiovascular parameter of the patient as may serve a particular implementation.

The plurality of measurements may be recorded one at a time over any predetermined time period that may serve a particular implementation. For example, the plurality of measurements may be scheduled to be recorded during waking hours of the patient during a single day, such as during the hours of a particular day when the patient is actually awake, during the hours of a particular day when many people are typically awake (e.g., from 6:00 AM until 10:00 PM), etc. Similarly, the plurality of measurements may be scheduled to be recorded during sleeping hours of the patient during a single day (or night), such as during the hours of the particular day or night when the patient is actually asleep, during the hours of the particular day or night when many people are typically asleep (e.g., from 10:00 PM until 6:00 AM), etc. In other examples, the plurality of measurements may be scheduled to be recorded during a consecutive 24-hour period such as from midnight until midnight, from 6:00 AM until 6:00 AM, etc.

In certain examples, all of the plurality of measurements may be scheduled to be taken automatically at designated times during the predetermined time period by a measuring device such as an automatic blood pressure monitor. For example, the plurality of measurements may be automatically recorded at scheduled times occurring at least twice per hour (e.g., every fifteen to thirty minutes) during waking hours of the patient, at least once per hour (e.g., ever thirty to sixty minutes) during sleeping hours of the patient, or at any other schedule times that may serve a particular implementation. Additionally or alternatively, such scheduled, automatic measurements may be combined with or replaced by manual measurements (e.g., measurements initiated by a person) that may be taken with similar frequencies as the automatic measurements described above or at whatever frequency and/or on whatever schedule may serve a particular implementation.

Data processing facility 402 may further be configured to compare the determined variability of the plurality of measurements of the cardiovascular parameter of the patient with a predetermined reference value. As will be described in more detail below, the variability of the plurality of measurements of the cardiovascular parameter may include a standard deviation of the plurality of measurements of the cardiovascular parameter of the patient or an index of variability value that may be calculated based on the standard deviation of the plurality of measurements. For example, the determined variability may be a standard deviation of blood pressure measurements of the patient taken during the waking hours of a single day or another predetermined time period. As such, if the determined variability is a standard deviation, the predetermined reference value with which data processing facility 402 compares the determined variability may represent a reference standard deviation selected based on a theoretical reference value, an analysis of the responsiveness to subcutaneous neuromodulation therapy of previously-treated patients, or any other criteria that may serve a particular implementation. Alternatively, if the determined variability is an index of variability value, the predetermined reference value with which data processing facility 402 compares the determined variability may represent a reference index of variability. Examples of variabilities and predetermined reference values compared by data processing facility 402 will be described in more detail below.

Data processing facility 402 may further be configured to designate the patient to be within a first class of patients or to be within a second class of patients based on the results of the comparison of the variability of the plurality of measurements and the predetermined reference value. For example, if the comparison indicates that the determined variability is less than the predetermined reference value, data processing facility 402 may designate the patient to be within the first class of patients, which may be representative of patients that are likely to be responsive to subcutaneous neuromodulation therapy as a treatment for hypertension. Designating the patient to be within the first class may include assigning (e.g., within patient classification data 408 of storage facility 404) the patient a first binary value (or any other suitable computer-readable value) representative of a determination by system 400 that the patient is likely to be responsive to the subcutaneous neuromodulation therapy as a treatment for hypertension. As described above, assigning the patient the first binary value may include associating a binary value (e.g., "TRUE") to a data field of a patient record. For example, within patient classification data 408, each patient may have a set of data fields including personal information, medical history, and so forth. Among the data fields may be a particular data field called "PREDICT_RE-SPONSIVENESS," which may be assigned a value of "TRUE" to indicate within system 400 that the patient is likely to be responsive to the subcutaneous neuromodulation therapy as a treatment for hypertension. Alternatively, assigning the patient the first binary value may include storing within a data structure maintained in patient classification data 408 (e.g., a data structure representing a list of patients predicted to be responsive to the therapy) an entry representative of the patient (e.g., including a name and/or another identifier associated with the patient).

In examples where the comparing indicates that the determined variability is greater than the predetermined reference value, data processing facility 402 may designate the patient to be within the second class of patients, which may be representative of patients that are likely to be unresponsive to subcutaneous neuromodulation therapy as a treatment for hypertension. Designating the patient to be within the second class may include assigning (e.g., within patient classification data 408 of storage facility 404) the patient a second binary value (or any other suitable computer-readable value) different than the first binary value and representative of a determination by system 400 that the patient is likely to be unresponsive to the subcutaneous neuromodulation therapy as a treatment for hypertension. As described above, assigning the patient the second binary value may include associating a binary value (e.g., "FALSE") with a data field of a patient record, such as the data field called "PREDICT_RESPONSIVENESS," described above. Alternatively, assigning the patient the second binary value may include storing within a data structure maintained in patient classification data 408 (e.g., a data structure representing a list of patients predicted to be unresponsive to the therapy) an entry representative of the patient (e.g., including a name and/or another identifier associated with the patient). In yet other examples, assigning the patient the second binary value may include simply not making an entry representative of the patient in the data structure representing the list of patients predicted to be responsive to the therapy described above.

Figure 5:
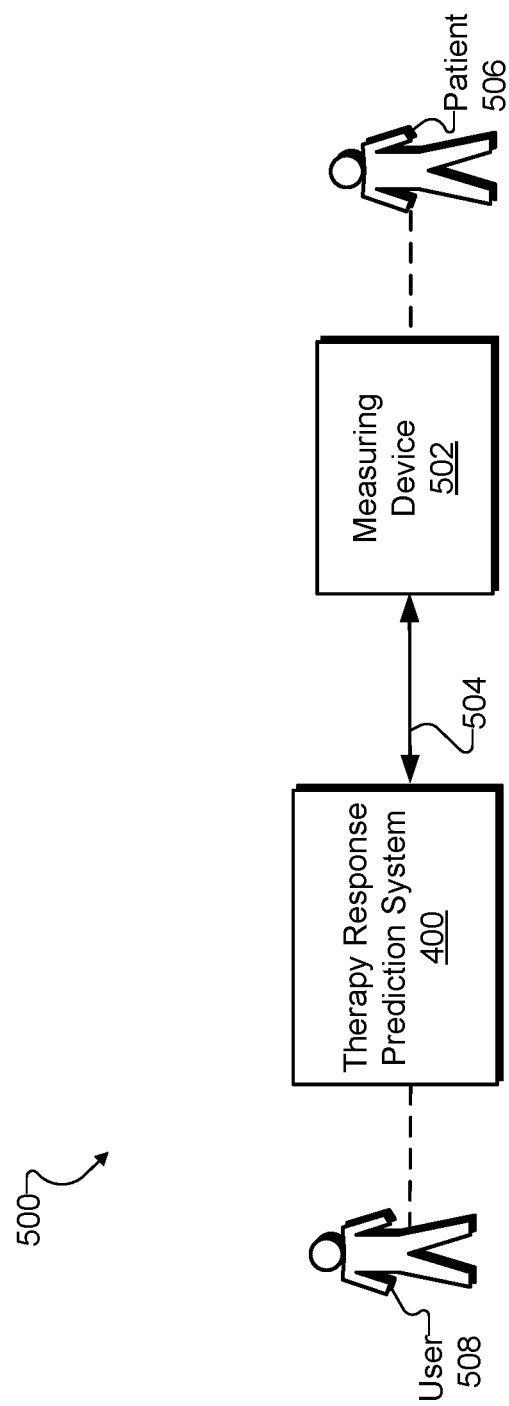
FIGS. 5-6 illustrate exemplary configurations in which the therapy response prediction system of FIG. 4 is used to predict the responsiveness of one or more patients to subcutaneous neuromodulation therapy as a treatment for the patients' hypertension according to principles described herein.

FIG. 5 illustrates an exemplary configuration 500 in which system 400 (described above in relation to FIG. 4) is used to predict the responsiveness of one or more patients to subcutaneous neuromodulation therapy as a treatment for the one or more patients' hypertension. As shown, configuration 500 may include therapy response prediction system 400 and a measuring device 502 separate from system 400. As shown, system 400 and measuring device 502 may be communicatively coupled by a communicative connection 504.

As described above, system 400 may be configured to determine a variability of a plurality of measurements of a cardiovascular parameter (e.g., blood pressure) of a patient suffering from hypertension after the measurements have been recorded one at a time over a predetermined time period (e.g., during waking hours of the patient during a single day). For examples, configuration 500 shows that system 400 may determine the variability of measurements of a cardiovascular parameter of a patient 506 by receiving a value representative of the variability from measuring device 502 by way of connection 504.

Specifically, measuring device 502 may be configured to record the plurality of measurements of the cardiovascular parameter of patient 506, calculate the value of the variability, and communicate the variability to system 400 (e.g., over connection 504). For example, measuring device 502 may be a sphygmomanometer (i.e., a blood pressure monitor) configured to automatically measure at least one of a systolic blood pressure, a diastolic blood pressure, a MAP, a pulse pressure, and a heart rate of patient 506 periodically (e.g., at least twice an hour during waking hours of patient 506 and/or at least once an hour during sleeping hours of patient 506) according to a schedule. As described above, in some examples measuring device 502 may additionally or alternatively be directed and/or controlled by a person to perform the measuring during the predetermined time period. Once measuring device 502 measures and records the plurality of measurements, measuring device 502 may calculate a value representative of the variability of the measurements by, for example, calculating a mean value of the measurements and/or calculating a standard deviation value of the measurements from the mean value. Subsequently, system 400 may determine the variability by simply receiving the standard deviation value of the measurements from measuring device 502 (e.g., by way of communication over connection 504) so that system 400 may compare the variability with a predetermined reference value representing a reference standard deviation and thereby designate patient 506 to be within a particular class, as described above in relation to FIG. 4.

In other examples, system 400 may be configured to determine the variability of the plurality of measurements of the cardiovascular parameter of patient 506 after the measurements have been recorded over the predetermined time period by receiving data representative of the plurality of measurements from measuring device 502 and by using the data to calculate a value representative of the variability.

Specifically, measuring device 502 may be configured to record the plurality of measurements of the cardiovascular parameter of patient 506 and communicate the measurements to system 400 (e.g., over connection 504). Thereafter, system 400 may determine the variability of the measurements by using the measurements to calculate the variability itself. For example, measuring device 502 may measure and record the plurality of measurements (e.g., blood pressure measurements, heart rate measurements, etc.) and send the measurements to system 400. In some examples, measuring device 502 may send (and system 400 may receive) data representative of the plurality of measurements subsequent to measuring device 502 subsequent to recording all of the plurality of measurements (e.g., after the predetermined time period has expired). Conversely, measuring device 502 may send (and system 400 may receive) data representative of the plurality of measurements in substantially real-time while measuring device 502 is recording the plurality of measurements (e.g., sent one at a time after each measurement is recorded, before the predetermined time period has expired). Upon receiving the measurements from measuring device 502, system 400 itself may calculate a value representative of the variability of the measurements by, for example, calculating a mean value of the measurements and/or calculating a standard deviation value of the measurements from the mean value. Subsequently, system 400 may compare the variability with a predetermined reference value representing a reference standard deviation and thereby designate patient 506 to be within a particular class, as described above in relation to FIG. 4.

System 400 and measuring device 502 may communicate with one another over connection 504 using any suitable communication technologies, devices, media, and protocols supportive of data communications, including, but not limited to, Universal serial bus ("USB"), Ethernet, data bus technologies, data transmission media, communication devices (e.g., portable flash drives), Transmission Control Protocol ("TCP"), Internet Protocol ("IP"), File Transfer Protocol ("FTP"), Telnet, Hypertext Transfer Protocol ("HTTP"), and other suitable communications technologies. In some examples, connection 504 may represent a network (e.g., a local area network ("LAN"), a wireless local area network ("WLAN"), the Internet, or any other suitable network). In other examples, connection 504 may represent a cable (e.g., a USB cable or a cable associated with another data transfer protocol) over which communication may be carried, or a separate device (e.g., a portable hard drive, portable flash drive, etc.) configured to transfer data by plugging into measuring device 502 to obtain and store data to be communicated and subsequently plugging into system 400 to transfer the stored data to system 400. In yet other examples, connection 504 may represent a manual transferring of data by a person. For example, measuring device 502 may output (e.g., on a display screen, on an LCD, on a paper printout, etc.) data that a person many manually input to system 400 (e.g., by typing on a keyboard associated with system 400).

In certain implementations, a user 508 may be associated with system 400. For example, user 508 may represent a personal practitioner associated with patient 506, a researcher associated with a study being conducted on subcutaneous neuromodulation therapy as a treatment for hypertension of which patient 506 is a participant, or any other person interested in predicting a responsiveness of patient 506 to subcutaneous neuromodulation therapy as a treatment for hypertension (e.g., patient 506 himself or herself). As such, system 400 may provide a graphical user interface (not explicitly shown) for use by user 508 for interfacing with system 400. The graphical user interface may be presented on a display screen associated with system 400. The graphical user interface may be used by user 508 to direct system 400 to perform any of the operations described above, such as determining the variability of the measurements of patient 506, comparing the variability with a predetermined reference value, and designating patient 506 to a first or a second class of patients representative of the likelihood of patient 506 to be responsive to subcutaneous neuromodulation therapy as a treatment for hypertension based on the comparison. The graphical user interface may also be used by user 508 to direct system 400 to perform any other operations that may serve a particular implementation.

In certain examples, the graphical user interface of system 400 may present to user 508 an indication that the patient is likely to be responsive to the subcutaneous neuromodulation therapy as a treatment for hypertension (i.e., if system 400 designated patient 506 to be within a first class of patients likely to be responsive to subcutaneous neuromodulation therapy as a treatment for hypertension). Similarly, the graphical user interface of system 400 may present to user 508 an indication that the patient is likely to be unresponsive to the subcutaneous neuromodulation therapy as a treatment for hypertension (i.e., if system 400 designated patient 506 to be within a second class of patients likely to be unresponsive to subcutaneous neuromodulation therapy as a treatment for hypertension).

In certain implementations, it may be desirable to predict patient responsiveness to subcutaneous neuromodulation therapy as a treatment for hypertension for a plurality of patients. For example, as discussed above, studies involving large numbers of patients may be conducted to demonstrate the effectiveness of subcutaneous neuromodulation therapy as a treatment for hypertension. In certain studies, for example, EA devices such as EA device 100 (described above in relation to FIG. 1) may be implanted into groups of patients suffering from hypertension to study the effects of subcutaneous neuromodulation therapy performed by the EA devices on the patients. These studies may be most effective and most likely to achieve their goals when only those patients who are likely to be responsive to subcutaneous neuromodulation therapy as a treatment for hypertension are included as subjects in the study. As such, system 400 may be used to screen patients likely to be responsive to the therapy from those likely to be unresponsive to the therapy during initial stages of setting up the study.

Figure 6:
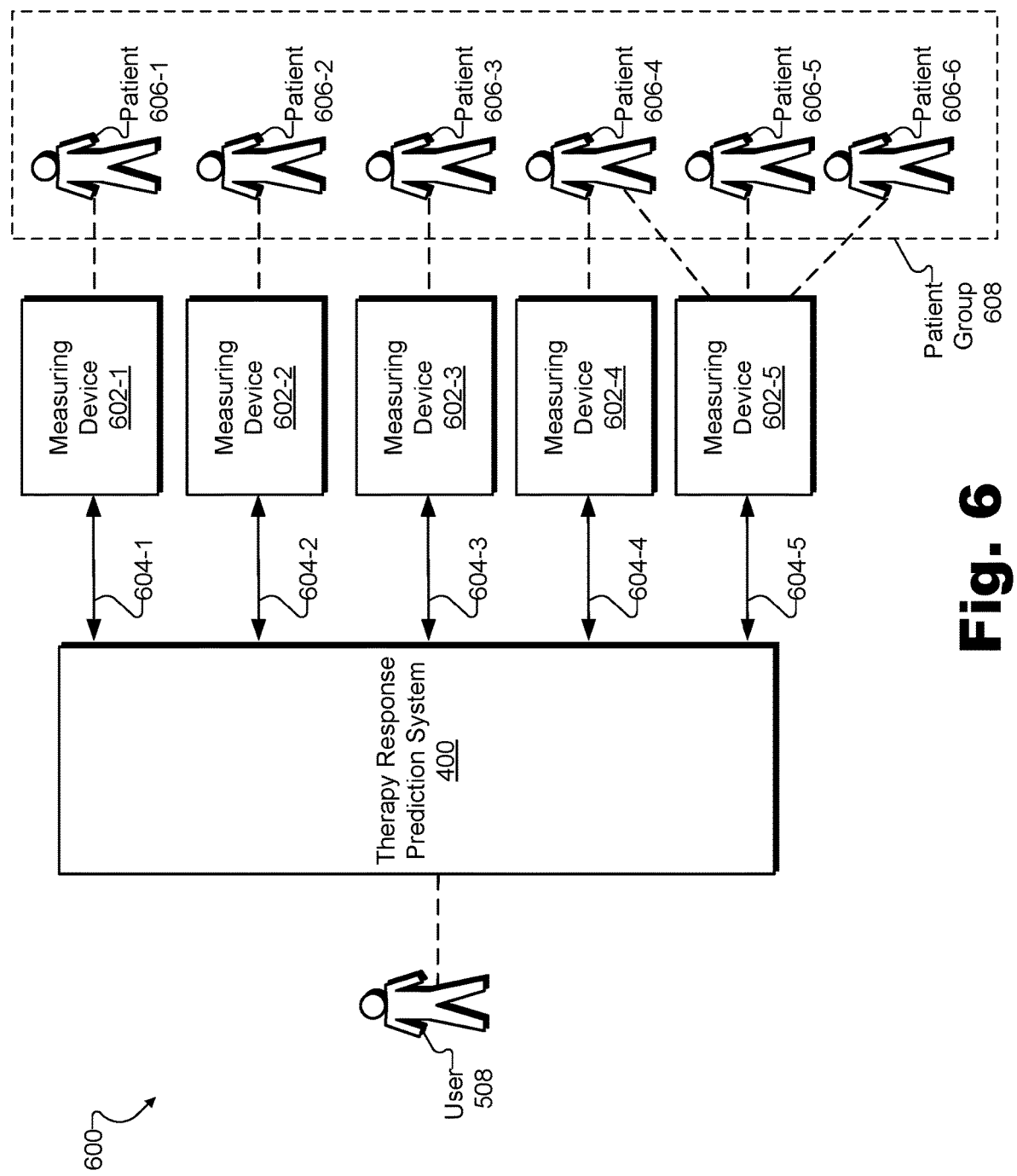

To illustrate, FIG. 6 illustrates an exemplary configuration 600 in which system 400 (described above in relation to FIG. 4) is used to predict the responsiveness of a plurality of patients to subcutaneous neuromodulation therapy as a treatment for the patients' hypertension. As shown, configuration 600 may include therapy response prediction system 400 and a plurality of measuring devices 602 (e.g., measuring devices 602-1 through 602-5) separate from system 400. As shown, system 400 may be communicatively coupled to each of measuring devices 602 by a plurality of communicative connections 604 (e.g., connections 604-1 through 604-5). While five measuring devices 602 and five connections 604 are illustrated in FIG. 6, it will be understood that any number of measuring devices 602 and connections 604 may be included in configuration 600 as may serve a particular implementation.

As described above, system 400 may be configured to determine a variability of a plurality of measurements of a cardiovascular parameter (e.g., blood pressure) from each of a plurality of patients suffering from hypertension after the measurements have been recorded one at a time over a predetermined time period (e.g., during waking hours of each of the patients during a single day). As illustrated by configuration 600, system 400 may determine the variability of each of a plurality of measurements of cardiovascular parameters of a plurality of patients 606 (e.g., patients 606-1 through 606-6) by receiving values representative of the variability of each of the plurality of measurements from measuring devices 602, or by receiving data representative of the measurements themselves from measuring device 602 and then calculating the variability values based on that data. While six patients 606 are illustrated in FIG. 6, it will be understood that any number of patients 606 may be included in configuration 600 as may serve a particular implementation.

Each of measuring devices 602 may be configured to record the plurality of measurements of the cardiovascular parameter of a patient 606 associated with the measuring device 602. For example, measuring device 602-1 may record the plurality of measurements of the cardiovascular parameter of patient 606-1, measuring device 602-2 may record the plurality of measurements of the cardiovascular parameter of patient 606-2, and so on.

While each of measuring devices 602-1 through 602-3 are shown in configuration 600 as being associated with exactly one patient 606 and each of patients 606-1 through 606-3 are shown as being associated with exactly one measuring device 602, it will be understood that measuring devices and patients may be associated with one another in any way that may serve a particular implementation. For example, a measuring device 602 may be associated with (e.g., used to measure cardiovascular parameters of) a plurality of patients 606, as illustrated by measuring device 602-5, which is used to measure cardiovascular parameters of patients 606-4, 606-5 and 606-6. Similarly, the cardiovascular parameters of one particular patient may be measured by a plurality of measuring devices 602 (e.g., during different portions of a predetermined time period during which the cardiovascular parameters are being measured). For example, patient 606-4 may be associated with both measuring device 602-4 (which may, for example, record measurements of patient 606-4 during waking hours) and measuring device 602-5 (which, for example, may record measurements of patient 606-4 during sleeping hours).

Moreover, while each of measuring devices 602 are illustrated in FIG. 6 to be simultaneously connected to system 400 over discrete connections 604, it will be understood that in certain implementations, each measuring device 602 may be connected to a single connection 604 at different times. For example, each measuring device 602 may be connected in turn (e.g., one at a time) to system 400 to transfer data representative of measurements of a cardiovascular parameter of a respective patient 606 after each measuring device 602 finishes recording the measurements for the respective patient 606.

As described above in relation to measuring device 502, each of measuring devices 602 may be a sphygmomanometer (i.e., a blood pressure monitor) configured to automatically measure at least one of a systolic blood pressure, a diastolic blood pressure, a MAP, a pulse pressure, and a heart rate of one of patients 606 periodically (e.g., at least twice an hour during waking hours of the patient 606 and/or at least once an hour during sleeping hours of the patient 606) according to a schedule. As described above, in some examples measuring devices 602 may additionally or alternatively be directed and/or controlled by a person to perform the measuring during the predetermined time period.

Once one of measuring devices 602 measures and records the plurality of measurements for a patient 606, the measuring device 602 may calculate a value representative of the variability of the measurements by, for example, calculating a mean value of the measurements and/or calculating a standard deviation value of the measurements from the mean value. Additionally or alternatively, the variability of the plurality of the measurements may be an index of variability value calculated by the measuring device 602. For example, an index of variability value may be calculated by: (1) calculating an average cardiovascular parameter of the patient 606 (e.g., an average systolic blood pressure, an average diastolic blood pressure, etc.) by averaging, over the predetermined time period (e.g., the waking hours of the patient 606), the plurality of measurements of the cardiovascular parameter of the patient, (2) calculating a standard deviation of the plurality of measurements, and (3) dividing the standard deviation by a square root of the average cardiovascular parameter. In certain embodiments, the measuring device 602 may simply communicate the plurality of measurements to system 400 (e.g., over the corresponding connection 604) and system 400 may calculate the variability value (e.g., the standard deviation or the index of variability) as described above. As example of calculating an index of variability will be described below.

In certain implementations, the determining of the variability of the plurality of measurements of the cardiovascular parameter of the patient may include normalizing a value representative of the variability to account for a bias of a measuring device used to record the plurality of measurements of the cardiovascular parameter of the patient. For example, measuring device 602-1 may have different characteristics (e.g., a different manufacturer, different calibration parameters, etc.) than measuring device 602-2 that may cause measuring device 602-1 to be biased to measure certain cardiovascular parameters (e.g., blood pressure) as being slightly higher than measuring device 602-2 would measure. Thus, to ensure that each of patients 606 are compared evenly to the predetermined reference value, system 400 may be configured to normalize measurements made by measuring device 602-1 in a downward direction (e.g., adjusting each measurement made by measuring device 602-1 to be lower by a particular factor associated with a known bias of measuring device 602-1) to be evenly compared with measurements made by measuring device 602-2. Alternatively, system 400 may be configured to normalize measurements made by measuring device 602-2 in an upward direction (e.g., adjusting each measurement made by measuring device 602-2 to be higher by a particular factor associated with a known bias of measuring device 602-2) to be evenly compared with measurements made by measuring device 602-1, to the same effect. In certain examples, the normalizing may be performed by one or more of measuring devices 602 rather than by system 400, or by both the measuring device 602 and by system 400 as may serve a particular implementation.

Whether system 400 determines variability values for each of patients 606 by receiving them from measuring devices 602 or by calculating the variability values itself, system 400 may compare each variability value with a predetermined reference value. For example, if the variability values represent standard deviations of each plurality of measurements, the predetermined reference value may represent a reference standard deviation. Alternatively, if the variability values each represent an index of variability calculated as described above, the predetermined reference value may represent a reference index of variability calculated by dividing a reference standard deviation by a square root of a group-averaged cardiovascular parameter. For example, patients 606 (as well as additional patients not shown) may belong to a patient group 608, which may include, for example, all of the patients participating in a particular study of patient responsiveness to subcutaneous neuromodulation therapy as a treatment for hypertension. A group-averaged cardiovascular parameter may generated by averaging a plurality of average cardiovascular parameters of members of patient group 608 (i.e., patients 606 and/or other patients within patient group 608). For example, the group-averaged cardiovascular parameter may be an average systolic blood pressure for all of the members of patient group 608 or for a subset of the members of patient group 608 (e.g., members of patient group 608 whose systolic blood pressure has already been measured and input into system 400).

Based on the comparison of the variability values and the predetermined reference values, system 400 may designate each patient 606 into either a first class of patients that are likely to be responsive to subcutaneous neuromodulation therapy as a treatment for hypertension, or a second class of patients that are likely to be unresponsive to subcutaneous neuromodulation therapy as a treatment for hypertension, as described above.

System 400 and measuring devices 602 may communicate with one another over one or more of connections 604 using any suitable communication technologies, devices, media, and protocols supportive of data communications, including, but not limited to, Universal serial bus ("USB"), Ethernet, data bus technologies, data transmission media, communication devices (e.g., portable flash drives), Transmission Control Protocol ("TCP"), Internet Protocol ("IP"), File Transfer Protocol ("FTP"), Telnet, Hypertext Transfer Protocol ("HTTP"), and other suitable communications technologies. In some examples, one or more of connections 604 may be combined into a single connection or may represent a network (e.g., a local area network ("LAN"), a wireless local area network ("WLAN"), the Internet, or any other suitable network. In some examples, one or more of connections 604 may represent a cable (e.g., a USB cable or a cable associated with another data transfer protocol) over which communication may be carried, or a separate device (e.g., a portable hard drive, portable flash drive, etc.) configured to transfer data by plugging into one of measuring devices 602 to obtain and store data to be communicated and subsequently plugging into system 400 to transfer the stored data to system 400. In yet other examples, one or more of connections 604 may represent a manual transferring of data by a person. For example, a particular measuring device 602 may output (e.g., on a display screen, on a LCD display, on a paper printout, etc.) data that a person many manually input to system 400 (e.g., by typing on a keyboard associated with system 400).

As described above in relation to FIG. 5, a user 508 may be associated with system 400. For example, user 508 may represent a personal practitioner associated with one or more of patients 606, a researcher associated with a study being conducted on subcutaneous neuromodulation therapy as a treatment for hypertension in which patients 606 are participating, or any other person interested in predicting a responsiveness of patients 606 to subcutaneous neuromodulation therapy as a treatment for hypertension (e.g., one or more of patients 606 themselves). User 508 may control and/or receive results from system 400 by way of a graphical user interface provided by system 400, as described above.

As described above, system 400 may predict patient responsiveness to subcutaneous neuromodulation therapy as a treatment for hypertension by determining a variability of a plurality of measurements of a cardiovascular parameter of a patient suffering from hypertension, the plurality of measurements recorded one at a time over a predetermined time period. As further described above, system 400 may additionally compare the determined variability with a predetermined reference value and designate the patient to be within a first or a second class of patients likely to be responsive or unresponsive to the therapy based on the comparison. To illustrate, FIGS. 7-9 show exemplary charts and distributions representative of exemplary measurements of cardiovascular parameters of patients to facilitate an understanding of these operations performed by system 400.

Figure 7:
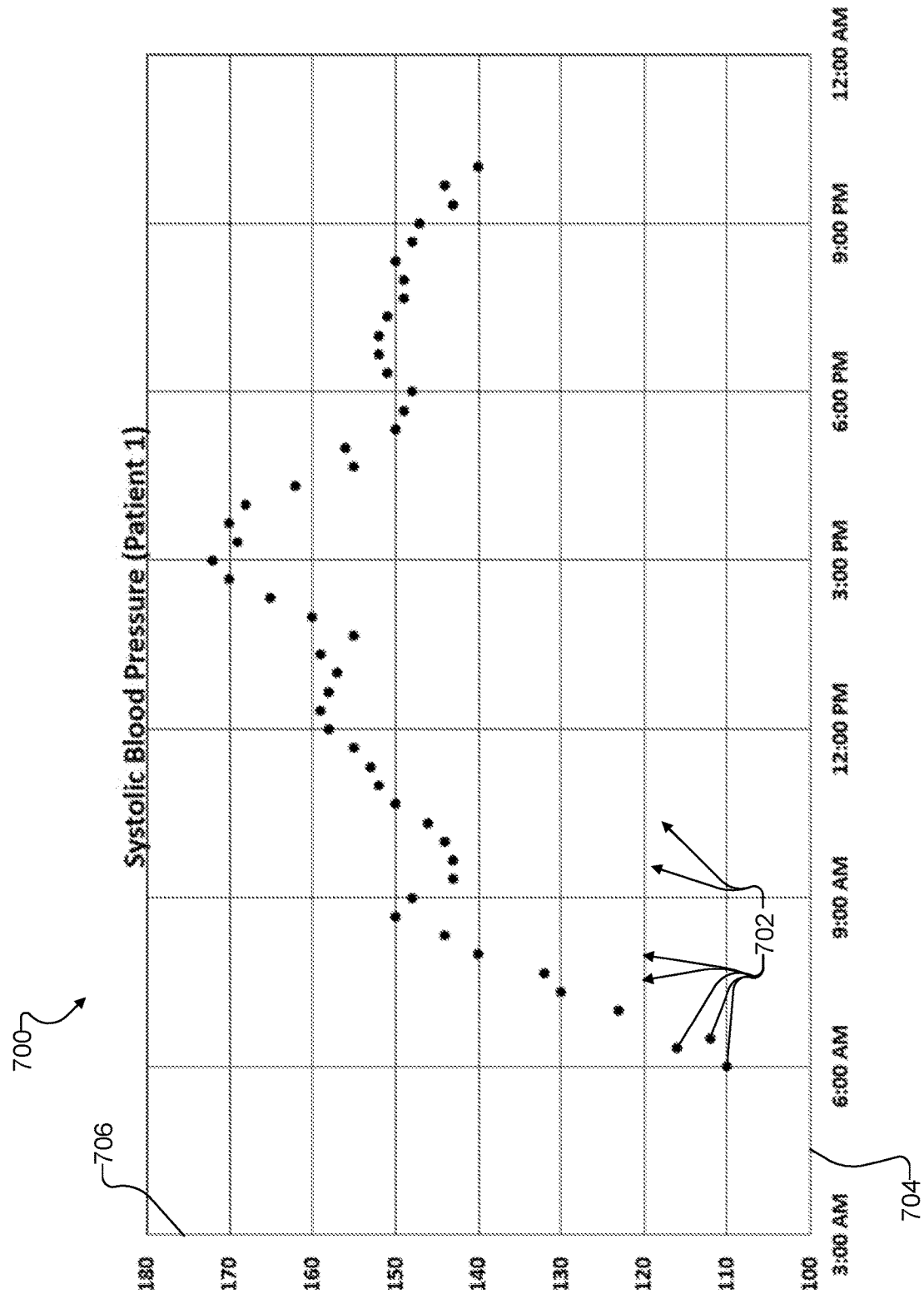
FIG. 7 illustrates an exemplary chart representative of a plurality of measurements of a cardiovascular parameter of a patient suffering from hypertension according to principles described herein.
Figure 8:
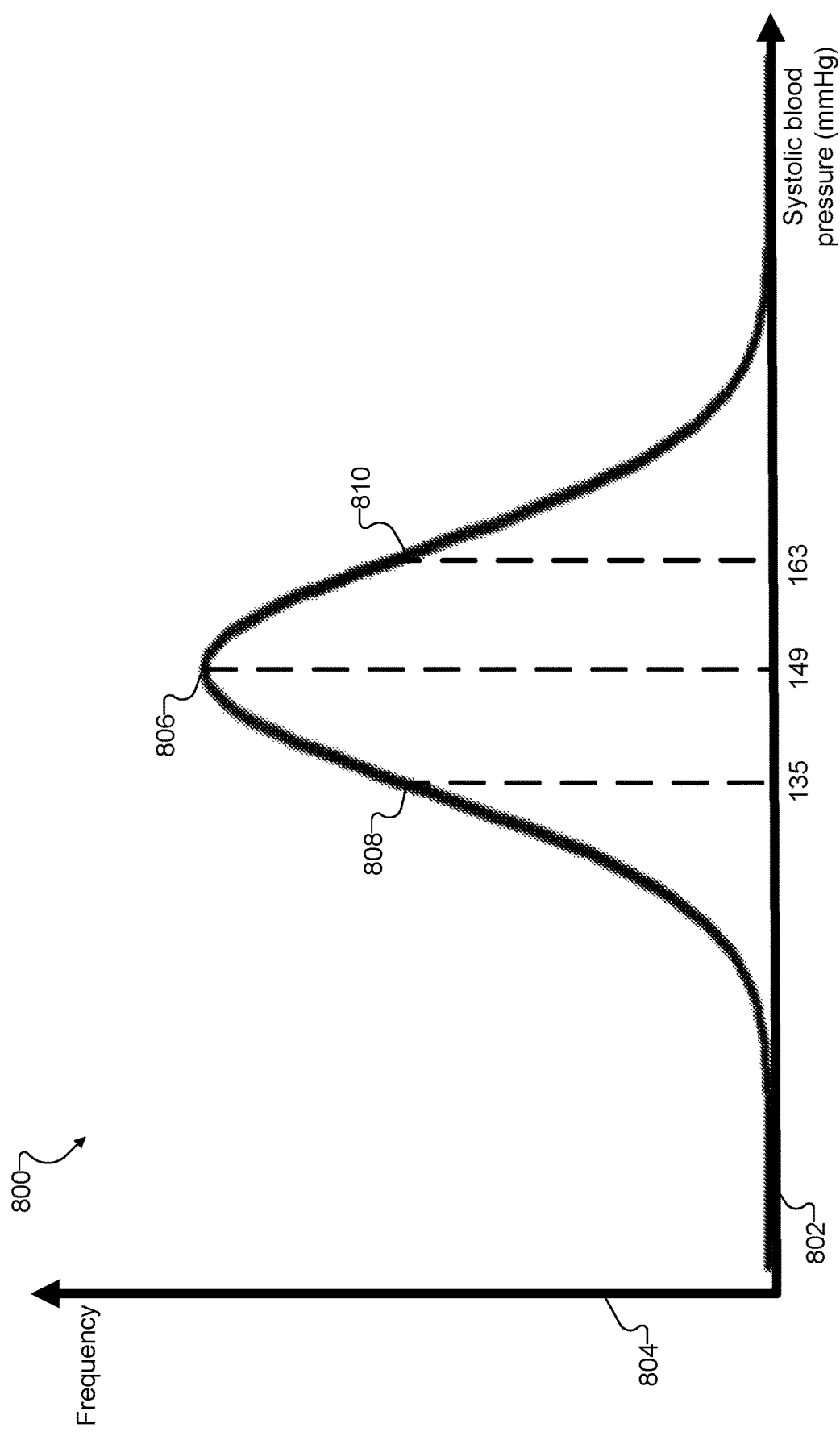
FIG. 8 illustrates an exemplary distribution of the plurality of measurements of the cardiovascular parameter of the patient illustrated in FIG. 7 according to principles described herein.

Specifically, FIG. 7 illustrates an exemplary chart 700 representative of a plurality of measurements 702 of a cardiovascular parameter of a patient suffering from hypertension. Chart 700 may illustrate measurements of any cardiovascular parameter that may serve a particular implementation. For example, as shown, chart 700 may show measurements of a systolic blood pressure of a particular patient (e.g., "patient 1") who may be a patient similar to patients 506 and 606 described above in relation to FIGS. 5 and 6.

As shown, measurements 702 (i.e., each of the black dots drawn on chart 700) may be charted on a horizontal time axis 704 and a vertical blood pressure axis 706. Time axis 704 may represent at least the time within a predetermined time period during which measurements 702 are recorded. For example, as shown, the predetermined time period may correspond to waking hours of the patient during a single day (e.g., from approximately 6:00 AM until approximately 10:00 PM). On chart 700, all of measurements 702 are recorded during the waking hours of the patient during the single day. However, it will be understood that additional or fewer measurements 702 may be recorded on chart 700 that may or may not be used by system 400 to designate the patient to be within the first or the second class. Additionally, the predetermined time period covered by time axis 704 may be longer or shorter than shown on chart 700. For example, the predetermined time period may include twenty four consecutive hours (e.g., from 6:00 AM one day until 6:00 AM the following day).

Measurements 700 may be scheduled to be recorded automatically or may be recorded manually at any times that may serve a particular implementation. For example, as shown in FIG. 7, at least some of measurements 702 may be recorded at scheduled times occurring at least twice per hour (e.g., every thirty minutes, every twenty minutes, every fifteen minutes, etc.) during the waking hours of the patient. In other examples, at least some of measurements 702 may be recorded at scheduled times occurring at least once per hour (e.g., every sixty minutes, every forty minutes, etc.) during sleeping hours of the patient within a twenty-four consecutive hour time period.

As illustrated, pressure axis 706 indicates what systolic blood pressure each measurement 702 represents. Pressure axis 706 indicates blood pressure in terms of any units that may serve a particular implementation. For example, on chart 700, pressure axis 706 may be labeled with blood pressure values representing measurements taken using millimeters of mercury ("mmHg") units. In other examples, pressure axis 706 may use other suitable units such as atmospheres or other units of pressure.

As described above, measurements 702 may be analyzed (e.g., by system 400 or by a measuring device separate from system 400 such as measuring device 502 of FIG. 5 or one of measuring devices 602 of FIG. 6) to determine an average cardiovascular parameter or a standard deviation of all the measurements. For example, system 400 and/or one of measuring devices 502 or 602 may calculate an average blood pressure of approximately 49 mmHg for "Patient 1" by calculating a mean value of all of measurements 702. Similarly, system 400 and/or one of measuring devices 502 or 602 may calculate a standard deviation of approximately 14 mmHg that measurements 702 deviate from the mean. An index of variability may also be calculated based on the mean and the standard deviation as described above. Specifically, the standard deviation (i.e., 14 mmHg) may be divided by a square root of the mean (i.e., the square root of 149 mmHg) to get an index of variability of approximately 1.1.

To illustrate, FIG. 8 shows an exemplary distribution 800 of measurements 702 of the systolic blood pressure of the patient (i.e., "patient 1"). As illustrated by distribution 800, measurements 702 may be approximately distributed according to a common distribution such as a Gaussian distribution. As such, distribution 800 is drawn on a horizontal blood pressure axis 802 and a vertical frequency axis 804. Because the measurement taken with the greatest frequency for the patient during the predetermined time period may be approximately equal to the mean, distribution 800 may be centered at measurement 806, which may correspond to approximately 149 mmHg. As shown, the first standard deviation (i.e., 14 mmHg greater than the mean and 14 mmHg less than the mean) may be bounded by measurement 808 (corresponding to approximately 135 mmHg), and by measurement 810 (corresponding to approximately 163 mmHg).

As further described above, once system 400 determines a variability value for the measurements (e.g., the standard deviation (i.e., 14 mmHg) or the index of variability (i.e., 1.1) of measurements 702), system 400 may compare the variability value to a predetermined reference value. For example, if the determined variability is a standard deviation, the predetermined reference used for the comparison may represent a reference standard deviation (e.g., a standard deviation between approximately 15 mmHg and 20 mmHg such as 18 mmHg). Conversely, if the determined variability is an index of variability calculated by dividing the standard deviation of measurements 702 by the square root of the mean measurement 702, the predetermined reference value may represent a reference index of variability calculated by dividing a reference standard deviation (e.g., 18 mmHg) by a square root of a group-averaged cardiovascular parameter (e.g., 156 mmHg). As described above, the group-averaged cardiovascular parameter may be generated by averaging a plurality of average cardiovascular parameters (e.g., mean blood pressures) of members of a group including a plurality of patients suffering from hypertension (e.g., such as patient group 608 of FIG. 6). Thus, for example, the reference index of variability may be calculated as 18 mmHg divided by the square root of 156 mmHg, or approximately 1.4.

Accordingly, for the patient whose blood pressure is represented by measurements 702 (i.e., "patient 1"), system 400 may compare the standard deviation of 14 mmHg to the reference standard deviation value of 18 mmHg, or may compare the index of variability of 1.1 with the reference standard deviation of 1.4. In either case, system 400 may determine from the comparison that the determined variability of measurements 702 is less than the predetermined reference value (i.e., because 14 mmHg is less than 18 mmHg, and 1.1 is less than 1.4). As a result, system 400 may designate the patient to a first class of patients representative of patients that are likely to be responsive to subcutaneous neuromodulation therapy as a treatment for hypertension rather than to a second class of patients that are likely to be unresponsive to the therapy.

FIG. 9 illustrates an exemplary summary chart 900 that summarizes, over several predetermined time periods, measurements of various cardiovascular parameters of a patient suffering from hypertension. In some examples, chart 900 may be generated (and, in some examples, displayed within a graphical user interface) by system 400 or by a measuring device (e.g., one of measuring devices 502 or 602) to summarize the cardiovascular health of the patient, and may be analyzed by the patient, a personal practitioner of the patient, and/or by a researcher studying the effects of subcutaneous neuromodulation therapy as a treatment for hypertension to help determine whether the patient should undergo the therapy. As shown in FIG. 9, chart 900 includes a summary of measurements taken by a measuring device (e.g., one of measuring devices 502 or 602) for a patient over a consecutive 24-hour period (section 902), during waking hours of the patient (section 904), and during sleeping hours of the patient (section 906). As shown, chart 900 may summarize any cardiovascular parameters that may serve a particular implementation, such as systolic blood pressure, diastolic blood pressure, MAP, pulse pressure, and heart rate of the patient. Chart 900 may include, for each cardiovascular parameter as part of the summary presented, an average ("AVG"), a standard deviation ("STD"), a minimum measurement value ("MIN"), and a maximum measurement value ("MAX"). Additionally, chart 900 may include, for each time period summarized (e.g., within each of sections 902, 904, and 906), a percentage of systolic blood pressure measurements that exceed a particular blood pressure limit such as 135 mmHg for waking hours of the patient and 120 mmHg for sleeping hours of the patient, and a percentage of diastolic blood pressure measurements that exceed a particular blood pressure limit such as 85 mmHg for waking hours of the patient and 70 mmHg for sleeping hours of the patient.

The examples above have focused on predicting patient responsiveness to subcutaneous neuromodulation therapy as a treatment for hypertension prior to implanting a subcutaneous neuromodulation therapy device (e.g., an EA device such as EA device 100) within the patient. For example, as described above, it is often useful to predict a patient's likely responsiveness to therapy prior to performing surgery to implant the device so that the patient can factor the likelihood that the therapy will be effective in treating the patient's hypertension into the decision about whether to undergo surgery to receive the implanted device.

However, it will be understood that methods and systems disclosed herein may also be useful even for patients who have already undergone surgery to receive an EA device to perform the subcutaneous neuromodulation therapy. For example, if an EA device implanted within a patient is only enabled when the patient's measured cardiovascular parameters indicate that the patient is likely to be responsive to subcutaneous neuromodulation provided by the EA device as treatment for the patient's hypertension, the battery life of the implanted device may be preserved rather than used during a period when the patient will likely be unreceptive to the therapy. Moreover, physical or psychological discomfort associated with the therapy may be avoided by foregoing the therapy during periods of time when the patient is likely to be unresponsive to the therapy.

Specifically, a disabled subcutaneous neuromodulation therapy device (e.g., an EA device that is disabled at the time of the implant surgery and remains disabled by default) may be implanted within a patient. Based upon a comparison of a determined variability and a predetermined reference value as described above, system 400 may be configured to automatically enable the disabled subcutaneous neuromodulation therapy device implanted within the patient if the patient is designated to be within the first class of patients likely to be responsive to the subcutaneous neuromodulation therapy as treatment for hypertension. Conversely, system 400 may be configured to avoid enabling (i.e., leaving disabled) the disabled subcutaneous neuromodulation therapy device implanted within the patient if the patient is designated to be within the second class of patients likely to be unresponsive to the subcutaneous neuromodulation therapy as treatment for the hypertension of the patient.

Figure 10:
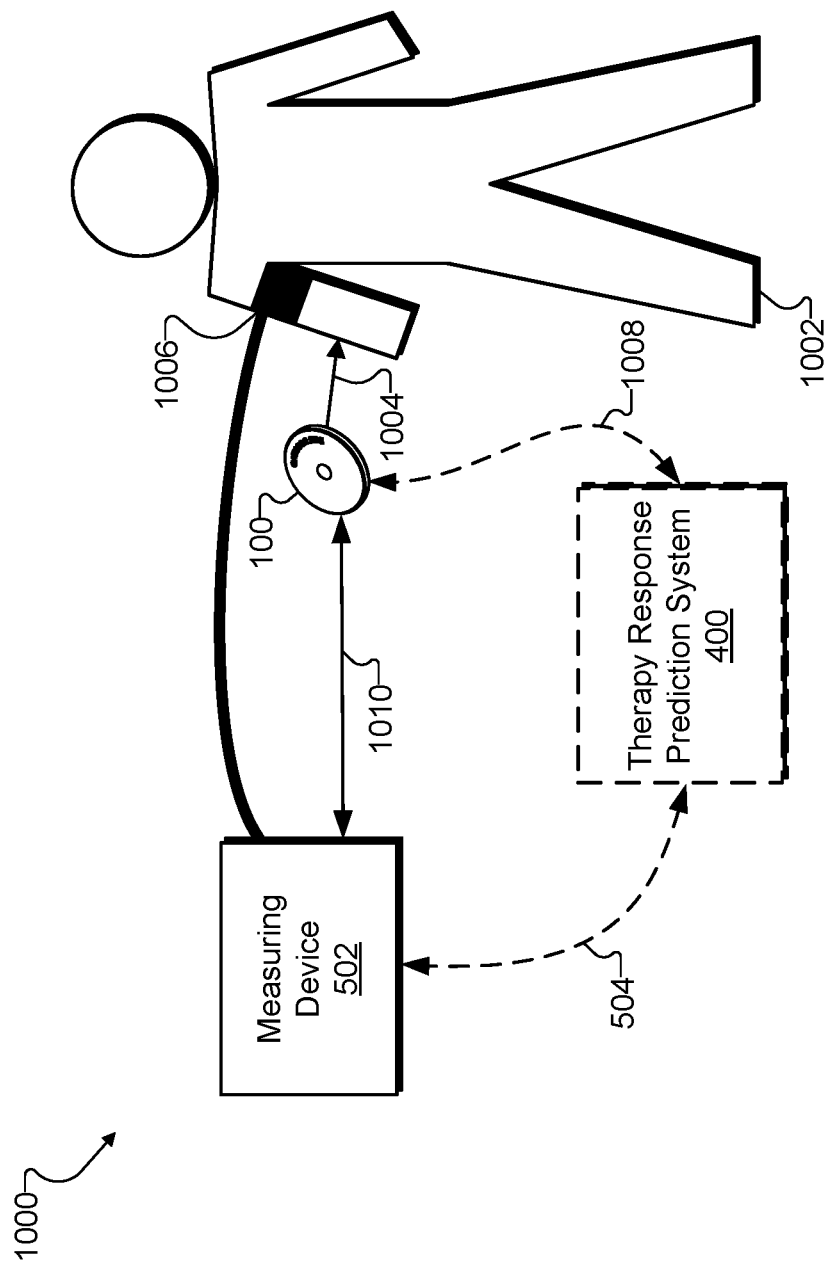
FIG. 10 illustrates an exemplary configuration in which the responsiveness of a patient to subcutaneous neuromodulation therapy as a treatment for hypertension is predicted and an electroacupuncture device implanted within the patient is automatically enabled or disabled based on the prediction according to principles described herein.

To illustrate, FIG. 10 shows an exemplary configuration 1000 in which the responsiveness of a patient 1002 to subcutaneous neuromodulation therapy as a treatment for hypertension is predicted and an electroacupuncture device implanted within the patient is automatically enabled or disabled based on the prediction. Specifically, as indicated by arrow 1004, patient 1002 may have undergone surgery to receive EA device 100 as an implant under the skin of the forearm of patient 1002.

After EA device 100 has been implanted, measuring device 502 (described above in relation to FIG. 5) may measure cardiovascular parameters (e.g., blood pressure) of patient 1002 using a device such as a blood pressure cuff 1006. Measuring device 502 may record measurements from patient 1002 and communicate the measurements and/or a variability value calculated from the measurements to system 400 over connection 504, described above in relation to FIG. 5. After performing operations described above to determine whether patient 1002 is likely to be responsive to subcutaneous neuromodulation therapy as a treatment for hypertension, system 400 may automatically enable EA device 100 to begin operation to treat the hypertension patient 1002 is suffering from if patient 1002 is determined to be likely to be responsive to the therapy and may avoid enabling EA device 100 (i.e. leaving it disabled) if patient 1002 is determined to be likely to be unresponsive to the therapy.

System 400 may communicate with EA device 100 (e.g., to enable EA device 100) over a communicative connection 1008 that uses any of the communication protocols or communication means described herein or any other communication means that may serve a particular implementation. For example, connection 1008 may include a wireless connection generated by a coil in system 400 or in a device associated with system 400 configured to communicate wirelessly through the skin of patient 1002 to transmit commands to EA device 100.

In certain examples, the operations described above as being performed by system 400 may be performed directly by measuring device 502, obviating the need for a stand-alone system 400 such as shown in configuration 1000. In other words, system 400 may be implemented within measuring device 502, which may be configured to communicate and transfer commands directly to EA device 100 over a communicative connection 1010, which may be similar or the same as connection 1008 described above or to any other communicative connection described herein. Accordingly, standalone system 400 and connections 504 and 1008 are illustrated with dashed lines in FIG. 10 to indicate that these are optional components of configuration 1000. In yet other embodiments, the operations described above may be performed by any combination of measuring device 502 and system 400 using any or all of connections 504, 1008, and 1010 as may serve a particular implementation.

Figure 11:
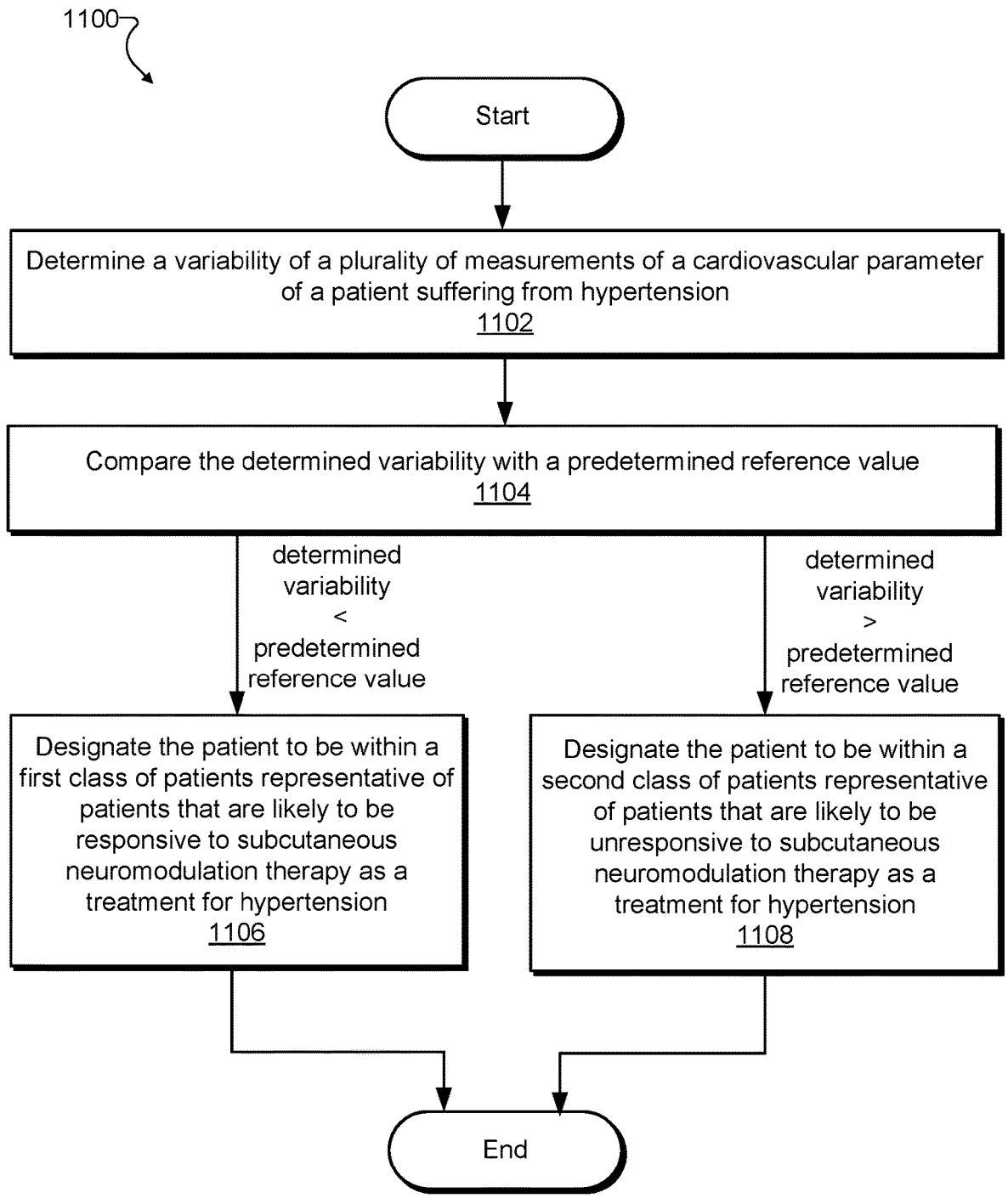
FIGS. 11-12 illustrate exemplary methods for predicting patient responsiveness to subcutaneous neuromodulation therapy as a treatment for hypertension according to principles described herein.

FIG. 11 illustrates an exemplary method 1100 for predicting patient responsiveness to subcutaneous neuromodulation therapy as a treatment for hypertension. While FIG. 11 illustrates exemplary operations according to one embodiment, other embodiments may omit, add to, reorder, and/or modify any of the operations shown in FIG. 11. One or more of the operations shown in FIG. 11 may be performed by system 400 and/or any implementation thereof.

In operation 1102, a therapy response prediction system determines a variability of a plurality of measurements of a cardiovascular parameter of a patient suffering from hypertension. In some examples, the plurality of measurements may be recorded one at a time over a predetermined time period. Operation 1102 may be performed in any of the ways described herein.

In operation 1104, the therapy response prediction system may compare the determined variability with a predetermined reference value. Operation 1104 may be performed in any of the ways described herein.

If the comparison performed in operation 1104 indicates that the determined variability is less than the predetermined reference value, method 1100 may proceed to operation 1106. In operation 1106, the therapy response prediction system may designate the patient to be within a first class of patients. In some examples, the first class of patients may be representative of patients that are likely to be responsive to subcutaneous neuromodulation therapy as a treatment for hypertension. Operation 1106 may be performed in any of the ways described herein.

Conversely, if the comparison performed in operation 1104 indicates that the determined variability is greater than the predetermined reference value, method 1100 may proceed to operation 1108. In operation 1108, the therapy response prediction system may designate the patient to be within a second class of patients. In some examples, the second class of patients may be representative of patients that are likely to be unresponsive to subcutaneous neuromodulation therapy as a treatment for hypertension. Operation 1108 may be performed in any of the ways described herein.

Figure 12:
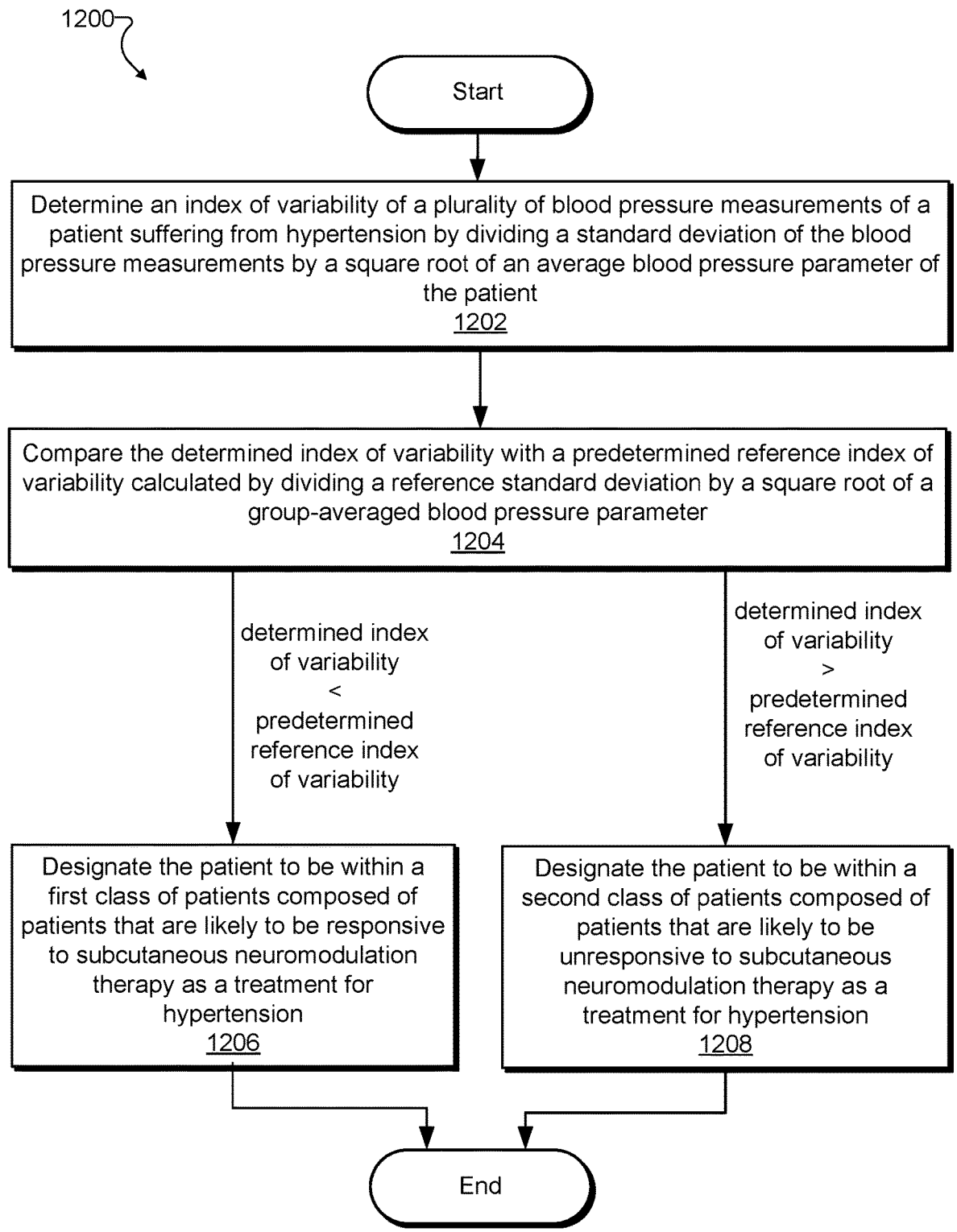

FIG. 12 illustrates another exemplary method 1200 of predicting patient responsiveness to subcutaneous neuromodulation therapy as a treatment for hypertension. While FIG. 12 illustrates exemplary operations according to one embodiment, other embodiments may omit, add to, reorder, and/or modify any of the operations shown in FIG. 12. One or more of the operations in FIG. 12 may be performed by system 400 and/or any implementation thereof.

In operation 1202, a therapy response prediction system may determine an index of variability of a plurality of blood pressure measurements of a patient suffering from hypertension. In some examples, the plurality of blood pressure measurements may be recorded one at a time during waking hours of the patient during a single day. Operation 1202 may be performed in any of the ways described herein. For example, the index of variability may be calculated by dividing a standard deviation of the plurality of blood pressure measurements of the patient by a square root of an average blood pressure parameter of the patient. The average blood pressure parameter may be generated by averaging, over the waking hours during the single day, the plurality of blood pressure measurements of the patient.

In operation 1204, the therapy response prediction system may compare the determined index of variability with a predetermined reference index of variability. In some examples, the predetermined reference index of variability may be calculated by dividing a reference standard deviation by a square root of a group-averaged blood pressure parameter. Operation 1204 may be performed in any of the ways described herein. For example, the group-averaged blood pressure parameter may be generated by averaging a plurality of average blood pressure parameters of members of a group including a plurality of other patients suffering from hypertension.

If the comparison performed in operation 1204 indicates that the determined index of variability is less than the predetermined reference index of variability, method 1200 may proceed to operation 1206. In operation 1206, the therapy response prediction system may designate the patient to be within a first class of patients. For example, the first class of patients may be composed of patients that are likely to be responsive to subcutaneous neuromodulation therapy as a treatment for hypertension. Operation 1206 may be performed in any of the ways described herein.

Conversely, if the comparison performed in operation 1204 indicates that the determined index of variability is greater than the predetermined reference index of variability, method 1200 may proceed to operation 1208. In operation 1208, the therapy response prediction system may designate the patient to be within a second class of patients. For example, the second class of patients may be composed of patients that are likely to be unresponsive to subcutaneous neuromodulation therapy as a treatment for hypertension. Operation 1208 may be performed in any of the ways described herein.

In certain embodiments, one or more of the systems, components, and/or processes described herein may be implemented and/or performed by one or more appropriately configured computing devices. To this end, one or more of the systems and/or components described above may include or be implemented by any computer hardware and/or computer-implemented instructions (e.g., software) embodied on at least one non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 13:
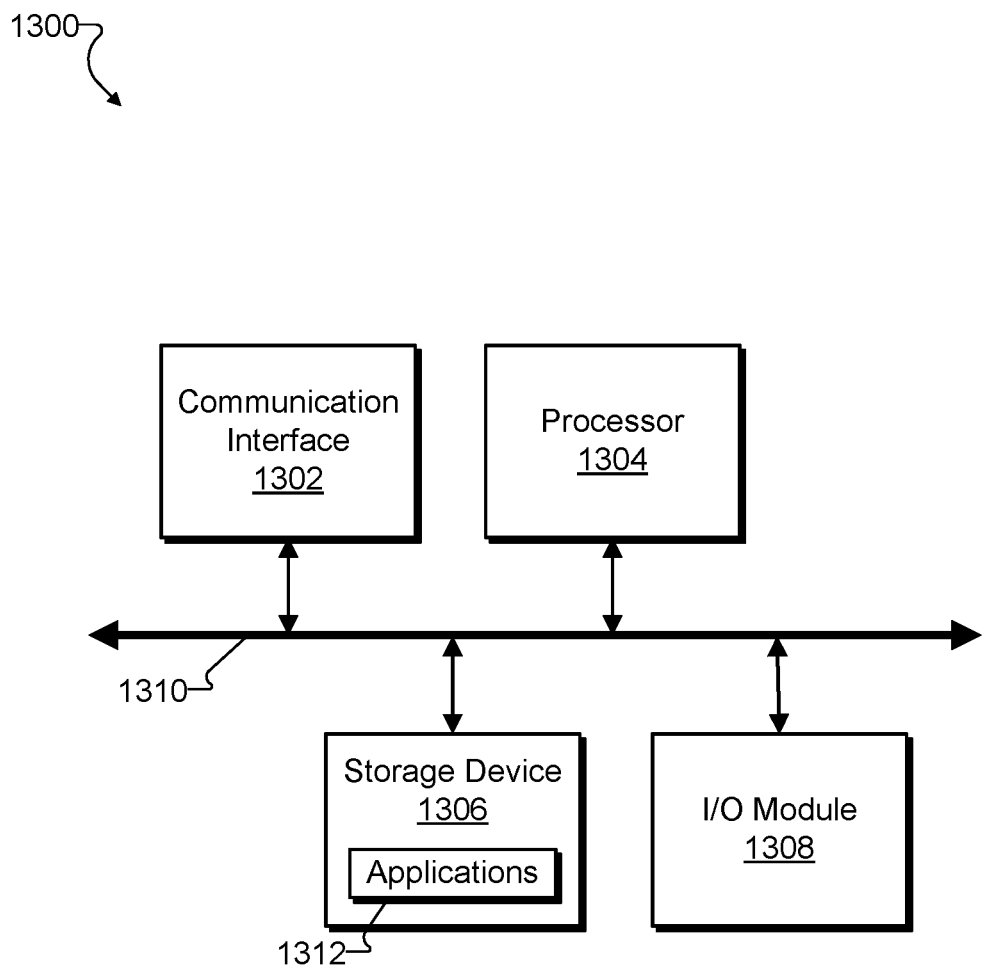
FIG. 13 illustrates an exemplary computing device according to principles described herein.

FIG. 13 illustrates an exemplary computing device 1300 that may be specifically configured to perform one or more of the processes described herein. As shown in FIG. 13, computing device 1300 may include a communication interface 1302, a processor 1304, a storage device 1306, and an input/output ("I/O") module 1308 communicatively connected via a communication infrastructure 1310. While an exemplary computing device 1300 is shown in FIG. 13, the components illustrated in FIG. 13 are not intended to be limiting. Additional or alternative components may be used in other embodiments. Components of computing device 1300 shown in FIG. 13 will now be described in additional detail.

Communication interface 1302 may be configured to communicate with one or more computing devices. Examples of communication interface 1302 include, without limitation, a wired network interface (such as a network interface card), a wireless network interface (such as a wireless network interface card), a modem, an audio/video connection, and any other suitable interface.

Processor 1304 generally represents any type or form of processing unit capable of processing data or interpreting, executing, and/or directing execution of one or more of the instructions, processes, and/or operations described herein. Processor 1304 may direct execution of operations in accordance with one or more applications 1312 or other computer-executable instructions such as may be stored in storage device 1306 or another computer-readable medium.

Storage device 1306 may include one or more data storage media, devices, or configurations and may employ any type, form, and combination of data storage media and/or device. For example, storage device 1306 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1306. For example, data representative of one or more executable applications 1312 configured to direct processor 1304 to perform any of the operations described herein may be stored within storage device 1306. In some examples, data may be arranged in one or more databases residing within storage device 1306.

I/O module 1308 may be configured to receive user input and provide user output and may include any hardware, firmware, software, or combination thereof supportive of input and output capabilities. For example, I/O module 1308 may include hardware and/or software for capturing user input, including, but not limited to, a keyboard or keypad, a touchscreen component (e.g., touchscreen display), a receiver (e.g., an RF or infrared receiver), and/or one or more input buttons.

I/O module 1308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1308 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1300. For example, one or more applications 1312 residing within storage device 1306 may be configured to direct processor 1304 to perform one or more processes or functions associated with data processing facility 402. Likewise, storage facility 404 may be implemented by or within storage device 1306.

To the extent the aforementioned embodiments collect, store, and/or employ personal information provided by individuals, it should be understood that such information shall be used in accordance with all applicable laws concerning protection of personal information. Additionally, the collection, storage, and use of such information may be subject to consent of the individual to such activity, for example, through well known "opt-in" or "opt-out" processes as may be appropriate for the situation and type of information. Storage and use of personal information may be in an appropriately secure manner reflective of the type of information, for example, through various encryption and anonymization techniques for particularly sensitive information.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
receiving, by a processor that is included within a therapy response prediction system and that is configured to execute instructions stored in a memory of the therapy response prediction system, a first plurality of blood pressure measurements recorded over a predetermined time period by a first automatic blood pressure monitor from a first patient suffering from hypertension and a second plurality of blood pressure measurements recorded over the predetermined time period by a second automatic blood pressure monitor from a second patient suffering from hypertension;
calculating, by the processor, a first blood pressure variability value representative of a variability of the first plurality of blood pressure measurements and a second blood pressure variability value representative of a variability of the second plurality of blood pressure measurements;
normalizing, by the processor, the first and second blood pressure variability values to account for different biases of the first and second automatic blood pressure monitors with respect to one another;
generating, by the processor, a predetermined reference value that is a group-averaged blood pressure variability parameter generated by averaging a plurality of blood pressure variability values that includes the first and second normalized blood pressure variability values;
comparing, by the processor, each of the first and second normalized blood pressure variability values with the predetermined reference value;
designating, by the processor in response to the comparing indicating that the first normalized blood pressure variability value is less than the predetermined reference value, the first patient to be within a first class of patients, the first class of patients representative of patients that are likely to be responsive to subcutaneous neuromodulation therapy as a treatment for hypertension;
designating, by the processor in response to the comparing indicating that the second normalized blood pressure variability value is greater than the predetermined reference value, the second patient to be within a second class of patients, the second class of patients representative of patients that are likely to be unresponsive to subcutaneous neuromodulation therapy as a treatment for hypertension;
providing, by the processor in response to the first patient being designated to be within the first class of patients, neuromodulation therapy to treat the hypertension of the first patient by automatically enabling a disabled subcutaneous neuromodulation therapy device implanted within the first patient; and
avoiding providing, by the processor in response to the second patient being designated to be within the second class of patients, the neuromodulation therapy to treat the hypertension of the second patient by abstaining from automatically enabling a disabled subcutaneous neuromodulation therapy device implanted within the second patient.

2. The method of claim 1, wherein the predetermined time period corresponds to waking hours of the patient during a single day.

3. The method of claim 2, wherein at least some of the first plurality of blood pressure measurements are recorded at scheduled times occurring at least twice per hour during the waking hours of the patient.

4. The method of claim 1, wherein the predetermined time period includes twenty-four consecutive hours.

5. The method of claim 4, wherein:
at least some of the first plurality of blood pressure measurements are recorded at scheduled times occurring at least twice per hour during waking hours of the patient within the twenty-four consecutive hours; and
at least some of the first plurality of blood pressure measurements are recorded at scheduled times occurring at least once per hour during sleeping hours of the patient within the twenty-four consecutive hours.

6. The method of claim 1, wherein the particular type of blood pressure measurements that the first and second automatic blood pressure monitors are configured to perform includes at least one of a systolic blood pressure and a diastolic blood pressure of the patient.

7. The method of claim 1, wherein:
the first blood pressure variability value is a standard deviation of the first plurality of blood pressure measurements of the patient; and
the predetermined reference value represents a reference standard deviation.

8. The method of claim 1, wherein:
the first blood pressure variability value of blood pressure measurements is an index of variability value calculated by dividing a standard deviation of the first plurality of blood pressure measurements of the first patient by a square root of an average blood pressure of the first patient, the average blood pressure of the first patient generated by averaging, over the predetermined time period, the first plurality of blood pressure measurements of the first patient; and
the predetermined reference value represents a reference index of variability calculated by dividing a reference standard deviation by a square root of a group-averaged blood pressure of a group including the first and second patients.

9. The method of claim 1, wherein:
the first automatic blood pressure monitor is separate from the therapy response prediction system;
the first automatic blood pressure monitor is configured to record the first plurality of blood pressure measurements of the first patient and calculate the first blood pressure variability value; and
the determining of the first blood pressure variability value includes receiving the first blood pressure variability value from the first automatic blood pressure monitor.

10. The method of claim 1, wherein:
the first automatic blood pressure monitor is separate from the therapy response prediction system; and
the determining of the first blood pressure variability value includes receiving, from the first automatic blood pressure monitor, data representative of the first plurality of blood pressure measurements, and using the data representative of the first plurality of blood pressure measurements to calculate the first blood pressure variability value.

11. The method of claim 1, wherein:

the designating of the first patient to be within the first class of patients includes assigning, within a storage facility of the therapy response prediction system, the first patient a first binary value representative of a determination by the processor that the first patient is likely to be responsive to the subcutaneous neuromodulation therapy as a treatment for hypertension; and the designating of the second patient to be within the second class of patients includes assigning, within the storage facility of the therapy response prediction system, the second patient a second binary value different than the first binary value and representative of a determination by the processor that the second patient is likely to be unresponsive to the subcutaneous neuromodulation therapy as a treatment for hypertension.

12. The method of claim 1, further comprising:

providing, by the processor for use by a user of the therapy response prediction system, a graphical user interface presented on a display screen associated with the therapy response prediction system;

presenting, by the processor within the graphical user interface in response to the first patient being designated to be within the first class of patients, an indication that the first patient is likely to be responsive to the subcutaneous neuromodulation therapy as a treatment for hypertension; and presenting, by the processor within the graphical user interface in response to the second patient being designated to be within the second class of patients, an indication that the second patient is likely to be unresponsive to the subcutaneous neuromodulation therapy as a treatment for hypertension.

13. The method of claim 1, embodied as computer-executable instructions on at least one non-transitory computer-readable medium.

14. A method comprising:

receiving, by a processor that is included within a therapy response prediction system and that is configured to execute instructions stored in a memory of the therapy response prediction system, a first plurality of blood pressure measurements recorded over a predetermined time period by a first automatic blood pressure monitor from a first patient suffering from hypertension and a second plurality of blood pressure measurements recorded over the predetermined time period by a second automatic blood pressure monitor from a second patient suffering from hypertension;

calculating, by the processor, a first index of variability of a first plurality of blood pressure measurements and a second index of variability of the second plurality of blood pressure measurements, the first index of variability calculated by dividing a standard deviation of the first plurality of blood pressure measurements of the first patient by a square root of an average blood pressure parameter of the first patient generated by averaging, over the waking hours during the single day, the first plurality of blood pressure measurements of the first patient;

normalizing, by the processor, the first and second indices of variability to account for different biases of the first and second automatic blood pressure monitors with respect to one another;

generating, by the processor, a predetermined reference index of variability that is calculated by dividing a reference standard deviation by a square root of a group-averaged blood pressure parameter, the group-averaged blood pressure parameter generated by averaging a plurality of average blood pressure parameters of members of a group including the first and second patients;

comparing, by the processor, each of the first and second normalized indices of variability with the predetermined reference index of variability;

designating, by the processor in response to the comparing indicating that the first normalized index of variability is less than the predetermined reference index of variability, the first patient to be within a first class of patients, the first class of patients composed of patients that are likely to be responsive to subcutaneous neuromodulation therapy as a treatment for hypertension;

designating, by the processor in response to the comparing indicating that the second normalized index of variability is greater than the predetermined reference index of variability, the second patient to be within a second class of patients, the second class of patients composed of patients that are likely to be unresponsive to subcutaneous neuromodulation therapy as a treatment for hypertension;

providing, by the processor in response to the first patient being designated to be within the first class of patients, neuromodulation therapy to treat the hypertension of the first patient by automatically enabling a disabled subcutaneous neuromodulation therapy device implanted within the first patient; and avoiding providing, by the processor in response to the second patient being designated to be within the second class of patients, the neuromodulation therapy to treat the hypertension of the second patient by abstaining from automatically enabling a disabled subcutaneous neuromodulation therapy device implanted within the second patient.

15. The method of claim 14, embodied as computer-executable instructions on at least one non-transitory computer-readable medium.

16. A system comprising:

a processor; and a memory communicatively coupled with the processor and storing instructions that, when executed by the processor, direct the processor to:

receive a first plurality of blood pressure measurements recorded over a predetermined time period by a first automatic blood pressure monitor from a first patient suffering from hypertension and a second plurality of blood pressure measurements recorded over the predetermined time period by a second automatic blood pressure monitor from a second patient suffering from hypertension;

calculate a first blood pressure variability value representative of a variability of the first plurality of blood pressure measurements and a second blood pressure variability value representative of a variability of the second plurality of blood pressure measurements;

normalize the first and second blood pressure variability values to account for different biases of the first and second automatic blood pressure monitors with respect to one another;

compare each of the first and second normalized blood pressure variability values with the predetermined reference value;

designate, in response to the comparison indicating that the first normalized blood pressure variability value is less than the predetermined reference value, the first patient to be within a first class of patients, the first class of patients representative of patients that are likely to be responsive to subcutaneous neuromodulation therapy as a treatment for hypertension;

designate, in response to the comparison indicating that the second normalized blood pressure variability value is greater than the predetermined reference value, the second patient to be within a second class of patients, the second class of patients representative of patients that are likely to be unresponsive to subcutaneous neuromodulation therapy as a treatment for hypertension;

provide, in response to the first patient being designated to be within the first class of patients, neuromodulation therapy to treat the hypertension of the first patient by automatically enabling a disabled subcutaneous neuromodulation therapy device implanted within the first patient; and avoid providing, in response to the second patient being designated to be within the second class of patients, the neuromodulation therapy to treat the hypertension of the second patient by abstaining from automatically enabling a disabled subcutaneous neuromodulation therapy device implanted within the second patient.

17. The system of claim 16, wherein:

the first blood pressure variability value is a standard deviation of the first plurality of blood pressure measurements of the patient; and the predetermined reference value represents a reference standard deviation.

18. The system of claim 16, wherein:

the first blood pressure variability value is an index of variability value calculated by dividing a standard deviation of the first plurality of blood pressure measurements of the first patient by a square root of an average blood pressure of the first patient, the average blood pressure of the first patient generated by averaging, over the predetermined time period, the first plurality of blood pressure measurements of the first patient; and the predetermined reference value represents a reference index of variability calculated by dividing a reference standard deviation by a square root of a group-averaged blood pressure of a group including the first and second patients.

19. The system of claim 16, wherein:

the predetermined time period corresponds to waking hours of the patient during a single day; and at least some of the first plurality of blood pressure measurements are recorded at scheduled times occurring at least twice per hour during the waking hours of the patient.

20. The system of claim 16, wherein:

the first automatic blood pressure monitor is separate from the system;

the first automatic blood pressure monitor is configured to record the first plurality of blood pressure measurements of the first patient and calculate the first blood pressure variability value; and the determining of the first blood pressure variability value includes receiving the first blood pressure variability value from the first automatic blood pressure monitor.

* * * * *